US009132234B2

(12) United States Patent
Estes et al.

(10) Patent No.: US 9,132,234 B2
(45) Date of Patent: Sep. 15, 2015

(54) INFUSION PUMP SYSTEMS AND METHODS

(71) Applicant: Bigfoot Biomedical, Inc., Milpitas, CA (US)

(72) Inventors: Mark C. Estes, Malibu, CA (US); Wenkang Qi, Cupertino, CA (US); Phillip Hopper, San Carlos, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 177 days.

(21) Appl. No.: 13/760,596

(22) Filed: Feb. 6, 2013

(65) Prior Publication Data

US 2013/0150824 A1 Jun. 13, 2013

Related U.S. Application Data

(63) Continuation of application No. 13/049,588, filed on Mar. 16, 2011, now Pat. No. 8,454,581.

(51) Int. Cl.
*A61K 9/22* (2006.01)
*A61M 5/172* (2006.01)
*A61M 5/142* (2006.01)
*A61M 5/168* (2006.01)
(Continued)

(52) U.S. Cl.
CPC ............ *A61M 5/172* (2013.01); *A61M 5/14244* (2013.01); *A61M 5/168* (2013.01); *A61M 5/1723* (2013.01); *G06F 19/3468* (2013.01); *A61M 5/1413* (2013.01); *A61M 2205/35* (2013.01); *A61M 2205/3569* (2013.01); *A61M 2205/3592* (2013.01); *A61M 2230/201* (2013.01)

(58) Field of Classification Search
CPC ........... G06F 19/3468; G06F 19/3406; A61M 5/14244; A61M 2205/50; A61M 5/1723; A61M 2205/3592; A61M 2230/201; A61M 5/1413
USPC ........................... 604/65–67, 189, 504, 890.1
See application file for complete search history.

(56) References Cited

U.S. PATENT DOCUMENTS

| 2,605,765 | A | 8/1952 | Kollsman |
| 3,886,938 | A | 6/1975 | Szabo et al. |
| 4,077,405 | A | 3/1978 | Haerten et al. |

(Continued)

FOREIGN PATENT DOCUMENTS

| CA | 2543545 | 5/2005 |
| DE | 196 27 619 A | 1/1998 |

(Continued)

OTHER PUBLICATIONS

International Search Report in International Application No. PCT/US2012/029225, Mailed Jun. 6, 2012, 12 pages.

(Continued)

*Primary Examiner* — Emily Schmidt
(74) *Attorney, Agent, or Firm* — Fish & Richardson P.C.

(57) ABSTRACT

Some embodiments of an infusion pump system can include a controller in which one or more features sets to be provided by the controller are enabled or disabled based upon the particular pump device that is connected to the controller. For example, in some embodiments, one or more advanced features of the controller are available to the user only when a first type of pump device (e.g., having predefined settings stored therein) is connected to the controller, and those advanced features of the controller are disabled when a second type of pump device is connected to the controller.

11 Claims, 11 Drawing Sheets

(51) Int. Cl.
    *G06F 19/00*    (2011.01)
    *A61M 5/14*     (2006.01)

(56)            References Cited

U.S. PATENT DOCUMENTS

| | | | |
|---|---|---|---|
| 4,231,368 A | 11/1980 | Becker |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,850,817 A | 7/1989 | Nason et al. |
| 5,045,064 A | 9/1991 | Idriss |
| 5,088,981 A | 2/1992 | Howson et al. |
| 5,190,522 A | 3/1993 | Wojcicki et al. |
| 5,261,882 A | 11/1993 | Sealfon |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,741,216 A | 4/1998 | Hemmingsen et al. |
| 5,772,635 A | 6/1998 | Dastur et al. |
| 5,816,306 A | 10/1998 | Giacomel |
| 5,852,803 A | 12/1998 | Ashby, III et al. |
| 5,873,731 A | 2/1999 | Prendergast |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |

(56) References Cited

U.S. PATENT DOCUMENTS

| | | | |
|---|---|---|---|
| 7,008,399 | B2 | 3/2006 | Larson et al. |
| 7,014,625 | B2 | 3/2006 | Bengtsson |
| 7,018,360 | B2 | 3/2006 | Flaherty et al. |
| 7,025,743 | B2 | 4/2006 | Mann |
| 7,029,455 | B2 | 4/2006 | Flaherty |
| 7,054,836 | B2 | 5/2006 | Christensen et al. |
| 7,104,972 | B2 | 9/2006 | Møller et al. |
| 7,133,329 | B2 | 11/2006 | Skyggebjerg et al. |
| 2001/0056262 | A1 | 12/2001 | Cabiri et al. |
| 2002/0004651 | A1 | 1/2002 | Ljndggreen et al. |
| 2002/0007154 | A1 | 1/2002 | Hansen et al. |
| 2002/0040208 | A1 | 4/2002 | Flaherty et al. |
| 2002/0091358 | A1 | 7/2002 | Klitmose |
| 2003/0055380 | A1 | 3/2003 | Flaherty |
| 2003/0088238 | A1 | 5/2003 | Poulsen et al. |
| 2003/0199825 | A1 | 10/2003 | Flaherty |
| 2003/0216683 | A1 | 11/2003 | Shekalim |
| 2004/0010207 | A1 | 1/2004 | Flaherty et al. |
| 2004/0019325 | A1 | 1/2004 | Shekalim |
| 2004/0064088 | A1 | 4/2004 | Gorman et al. |
| 2004/0064096 | A1 | 4/2004 | Flaherty et al. |
| 2004/0078028 | A1 | 4/2004 | Flaherty et al. |
| 2004/0087894 | A1 | 5/2004 | Flaherty |
| 2004/0092865 | A1 | 5/2004 | Flaherty et al. |
| 2004/0092878 | A1 | 5/2004 | Flaherty |
| 2004/0116866 | A1 | 6/2004 | Gorman et al. |
| 2004/0127844 | A1 | 7/2004 | Flaherty |
| 2004/0153032 | A1 | 8/2004 | Garribotto et al. |
| 2004/0176727 | A1 | 9/2004 | Shekalim |
| 2004/0204673 | A1 | 10/2004 | Flaherty |
| 2004/0220551 | A1 | 11/2004 | Flaherty et al. |
| 2004/0235446 | A1 | 11/2004 | Flaherty et al. |
| 2004/0260233 | A1 | 12/2004 | Garibotto et al. |
| 2005/0021005 | A1 | 1/2005 | Flaherty et al. |
| 2005/0022274 | A1 | 1/2005 | Campbell et al. |
| 2005/0065760 | A1 | 3/2005 | Murtfeldt et al. |
| 2005/0090808 | A1 | 4/2005 | Malave et al. |
| 2005/0095063 | A1 | 5/2005 | Fathallah et al. |
| 2005/0160858 | A1 | 7/2005 | Mernoe |
| 2005/0171512 | A1 | 8/2005 | Flaherty |
| 2005/0182366 | A1 | 8/2005 | Vogt et al. |
| 2005/0192561 | A1 | 9/2005 | Mernoe |
| 2005/0203461 | A1 | 9/2005 | Flaherty et al. |
| 2005/0215982 | A1 | 9/2005 | Malave et al. |
| 2005/0222645 | A1 | 10/2005 | Malave et al. |
| 2005/0238507 | A1 | 10/2005 | DiIanni et al. |
| 2005/0245878 | A1 | 11/2005 | Mernoe et al. |
| 2005/0251097 | A1 | 11/2005 | Mernoe |
| 2005/0273059 | A1 | 12/2005 | Mernoe et al. |
| 2005/0277890 | A1 | 12/2005 | Stewart et al. |
| 2006/0041229 | A1 | 2/2006 | Garibotto et al. |
| 2006/0069382 | A1 | 3/2006 | Pedersen |
| 2006/0074381 | A1 | 4/2006 | Malave et al. |
| 2006/0095014 | A1 | 5/2006 | Ethelfeld |
| 2006/0135913 | A1 | 6/2006 | Ethelfeld |
| 2006/0142698 | A1 | 6/2006 | Ethelfeld |
| 2006/0178633 | A1 | 8/2006 | Garibotto et al. |
| 2006/0184119 | A1 | 8/2006 | Remde et al. |
| 2006/0200073 | A1 | 9/2006 | Radmer et al. |
| 2006/0206054 | A1 | 9/2006 | Shekalim |
| 2006/0247581 | A1 | 11/2006 | Pedersen et al. |
| 2007/0156092 | A1 | 7/2007 | Estes et al. |
| 2008/0294142 | A1 | 11/2008 | Patel et al. |
| 2009/0118664 | A1 | 5/2009 | Estes et al. |
| 2009/0143916 | A1 | 6/2009 | Boll et al. |

FOREIGN PATENT DOCUMENTS

| | | |
|---|---|---|
| DE | 102 36 669 A | 2/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |

OTHER PUBLICATIONS

International Preliminary Report on Patentability in International Application No. PCT/US2012/029225, Mailed Sep. 26, 2013, 8 pages.

Authorized Officer Cezary Chabros, International Search Report for International Application No. PCT/US2012/029225, dated Jun. 6, 2012, 12 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Medtronic News Release, "Medtronic Receives FDA Approval for World's First Insulin Pump with Real-time Continuous Glucose Monitoring," Apr. 13, 2006, 3 pages.

'Minimed Inc. Introduces 407C Infusion Pump for General Medication Use' [online]. Business Wire, AllBusiness.com, Aug. 10, 1999 [retrieved on Feb. 28, 2011]. Retrieved from the Internet: <URL: http://www.allbusiness.com/company-activities-management/product-management/6734565-1.html>.

INFUSION PUMP SYSTEMS AND METHODS

CROSS-REFERENCE TO RELATED APPLICATION(S)

This is a continuation of U.S. patent application Ser. No. 13/049,588 filed on Mar. 16, 2011, the entire contents of this previous application being incorporated herein by reference.

TECHNICAL FIELD

This document relates to a portable infusion pump system, such as a wearable insulin pump system that delivers dosages of a medication to a user over an extended period of time.

BACKGROUND

Pump devices are commonly used to deliver one or more fluids to a targeted individual. For example, a medical infusion pump may be used to deliver a medicine to a patient as part of a medical treatment. The medicine that is delivered by the infusion pump can depend on the condition of the patient and the desired treatment plan. For example, infusion pumps have been used to deliver insulin to diabetes patients so as to regulate blood-glucose levels. In another example, infusion pumps have been used to deliver pain medication to patients suffering from chronic or degenerative conditions so as to reduce pain symptoms and increase comfort.

In some circumstances, the infusion pumps can be equipped with user interface components, internal circuitry and components that offer additional feature sets to the user. For example, some infusion pumps are configured for delivery of insulin can be equipped with circuitry and communication devices that provide additional features sets such as wireless interaction with continuous glucose monitoring (CGM) sensors or wireless interaction with blood glucose meters. Some of these infusion pumps may be configured in a manner so that these additional feature sets are generally enabled at all times.

SUMMARY

Some embodiments of an infusion pump system can include a controller in which one or more features sets to be provided by the controller are enabled or disabled based upon the particular pump device that is connected to the controller. For example, the controller can be configured to removably attach with any one of a plurality of pump devices having different pump settings (e.g., set by the supplier), and the controller may enable particular features of the controller when a first type of pump device is attached therewith or may disable those particular features of the controller when a second type of pump device is attached therewith. Thus, in some embodiments, one or more advanced features of the controller are available to the user only when a first type of pump device (e.g., having predefined settings stored therein) is connected to the controller, and those advanced features of the controller are disabled when a second type of pump device is connected to the controller.

In particular embodiments, a portable infusion pump system may include a pump device and a controller device. The pump device may include a pump housing that defines a space to receive a medicine and a drive system to dispense the medicine from the pump device when the medicine is received in the space of the pump housing. The controller device may be removably attachable to the pump device so as to electrically connect with the pump device and control dispensation of the medicine from the pump device. The controller device may automatically disable a first feature set provided by the controller device in response to electrical connection with the pump device.

Some embodiments described herein include a method of using a portable infusion pump system. The method may include removably attaching a pump device to a controller device to form an electrical connecting between the controller device and the pump device so that the controller device is operable to control dispensation of medicine from the pump device. The controller device may automatically disable an advanced feature set provided by the controller device in response to electrical connection with the pump device. The method may also include operating a user interface of the controller device.

Other embodiments may include a method of controlling a portable infusion pump system. The method may include querying a pump device to determine if the pump device is a first type of pump device or a second type of pump device. The pump device may be removably attached to a controller device to form an electrical connecting between the controller device and the pump device so that the controller device is operable to control dispensation of medicine from the pump device. The method may also include automatically disabling a first feature set provided by the controller device in response to the controller device recognizing that the pump device is the second type of pump device.

In some embodiments, a portable infusion pump system may include a pump device and a controller device. The pump device may include a pump housing that defines a space to receive a medicine and a drive system to dispense the medicine from the pump device when the medicine is received in the space of the pump housing. The controller device may be removably attachable to the pump device so as to electrically connect with the pump device and control dispensation of the medicine from the pump device. The controller device may be configured to automatically enable a first feature set provided by the controller device in response to the controller device recognizing that the pump device is a first type of pump device. Also, the controller device may be configured to automatically disable the first feature set provided by the controller device in response to the controller device recognizing that the pump device is a second type of pump device.

Some or all of the embodiments described herein may provide one or more of the following advantages. First, some embodiments of the infusion pump system may include a configuration in which one or more advanced features of a controller device are automatically activated or made available to the user only in response to a particular type of pump device being connected to the controller device. Also, the controller device may disable the advanced features in the event that a second type of pump device is connected to the controller device.

Second, is certain embodiments, the controller device of the infusion pump system can be configured to removably attach with any one of plurality of different types of pump devices. In such circumstances, the controller device may be configured as a reusable controller that is repeatedly used with a series of disposable pump devices over an extended period of time.

Third, in some embodiments, each of the different types of pump devices can include a selected setting (e.g., stored in a memory device) that is established by the supplier so as to define the type of pump device. In such circumstances, the supplier can dictate which pump devices will enable additional feature sets of the controller device and which other pump devices will disable the additional feature sets of the controller device.

Fourth, using techniques discussed herein, some embodiments of the controller device may automatically activate advanced features related to CGM (e.g., wireless communication with a continuous glucose sensor, user interface display of CGM data, and the like) only in response to an advanced type of pump device being connected to the controller device. For example, the advanced type of pump device may include a parameter setting stored in an internal memory device that is detected by the controller device, which in turn causes the controller device to make available to the user the advanced feature set related to CGM. Conversely, the controller device may disable advanced features related to CGM in response to a basic type of pump device being connected to the controller device. In this example, the basic type of pump device may include a different parameter setting stored in an internal memory device that is detected by the controller device, which in turn causes the controller device to remove availability of the advanced feature set related to CGM (e.g., disable the wireless communication device to increase battery life, provide reduced user interface options and menus, and the like).

Fifth, some embodiments of the controller device may automatically activate advanced features related to communication with a blood glucose meter (e.g., wireless communication with a blood test strip reader, advanced bolus calculation options, and the like) only in response to an advanced type of pump device being connected to the controller device. In these embodiments, the controller device may disable advanced features related to communication with a blood glucose meter in response to a basic type of pump device being connected to the controller device. In this example, the basic type of pump device may include a different parameter setting stored in an internal memory device that is detected by the controller device, which in turn causes the controller device to remove availability of the advanced feature set related to communication with a blood glucose meter.

Sixth, some embodiments of the controller device may automatically activate a feature set related to a "training mode" only in response to a training type of pump device being connected to the controller device. The feature set related to the training mode may permit a new user to practice using the infusion pump system (e.g., setting dosage programs, responding to alarms, and the like) without actually receiving medicine dispensation from the infusion pump system or with delivering medicine in accordance with a basic dosage schedule. For example, the training type of pump device may include a parameter setting stored in an internal memory device that is detected by the controller device, which in turn causes the controller device to make available to a set of basic menu options that train the user to use the infusion pump system while the drive system is disabled (e.g., no medication is delivered) or while the drive system delivers medicine in accordance with a basic dosage schedule. In these embodiments, the controller device may disable the features related to the training mode and enable other features in which the pump system is activated to deliver medicine (e.g., operate in a normal mode with multiple basal profile options and bolus delivery options) in response to a different type of pump device being connected to the controller device.

Sixth, some embodiments of the controller device may automatically activate selected features related to a first medicine type (e.g., a user interface and dosage options related to insulin delivery) only in response to a first type of pump device being connected to the controller device. For example, the first type of pump device may include a medicine type parameter stored in an internal memory device that is detected by the controller device, which in turn causes the controller device to make available to the user the specific user interface and dosage options related to insulin delivery. Conversely, the controller device may disable selected features related to insulin delivery in response to a second type of pump device being connected to the controller device. In this example, the second type of pump device may include a different medicine type parameter setting stored in an internal memory device that is detected by the controller device, which in turn causes the controller device to remove availability of the selected features related to insulin delivery and instead activate different user interface and dosage options related to a different medicine. Thus, the controller can be configured to control dosages of multiple different types of medicines, and the controller's user interface and dosage options can be automatically adjusted based upon the particular type of pump device that is connected therewith.

The details of one or more embodiments are set forth in the accompanying drawings and the description below. Other features, objects, and advantages will be apparent from the description and drawings, and from the claims.

DETAILED DESCRIPTION OF ILLUSTRATIVE EMBODIMENTS

Figure 1:
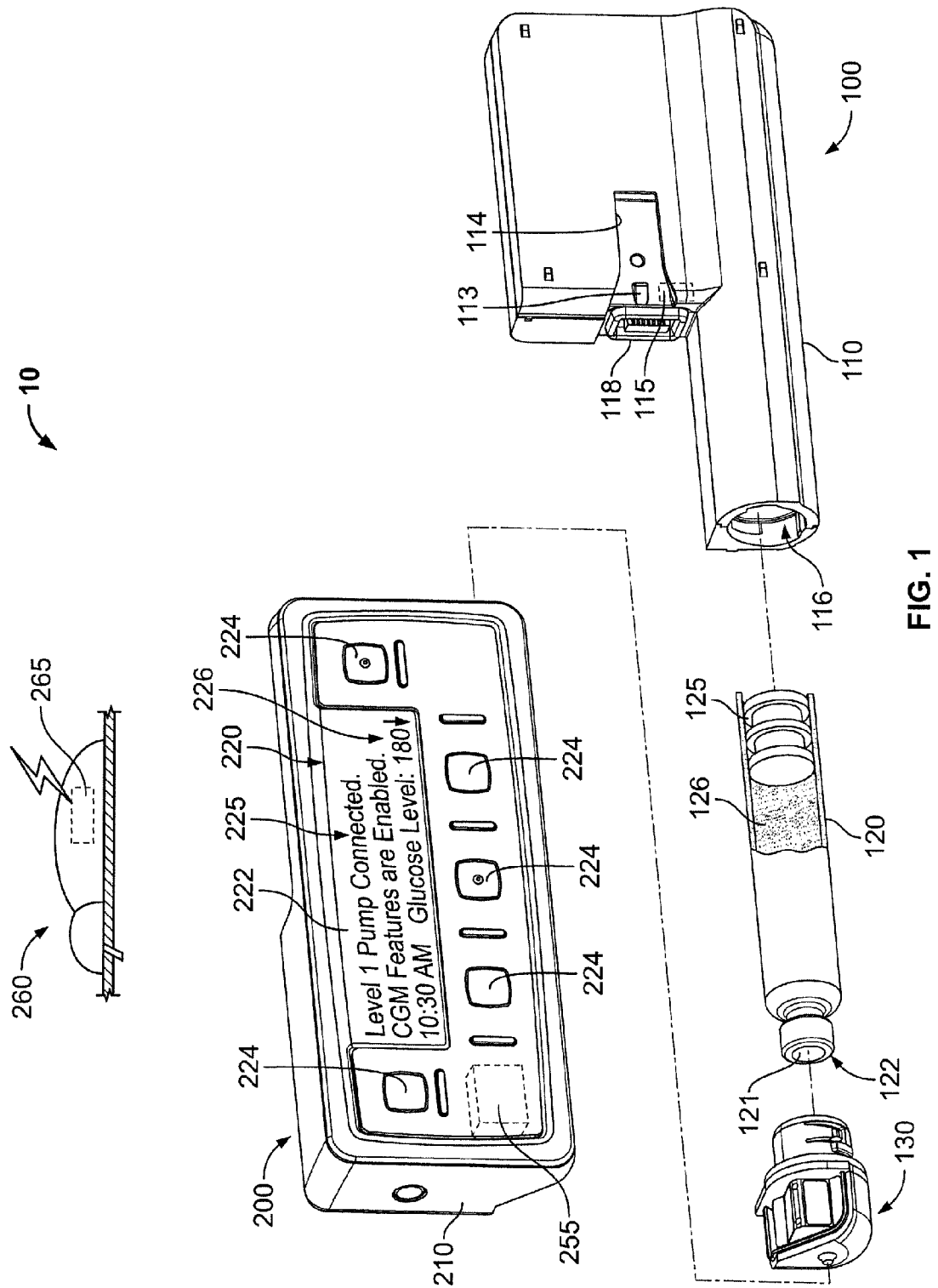
FIG. 1 is a perspective view of an infusion pump system in accordance with some embodiments.

Referring to FIG. 1, an infusion pump system 10 can include a pump device 100 and a controller device 200 that communicates with the pump device 100. The pump device 100 in this embodiment includes a housing structure 110 that defines a cavity 116 in which a fluid cartridge 120 can be received. The fluid cartridge 120 may contain insulin or another medicine as described in more detail below. The pump device 100 also can include a cap device 130 to retain the fluid cartridge 120 in the cavity 116 of the housing structure 110. The pump device 100 can include a drive system 300 (described in connection with FIG. 8) that advances a plunger 125 in the fluid cartridge 120 so as to dispense fluid therefrom. The controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing, in a pouch clipped at the waist (e.g., similar to a cell phone pouch), or in the user's pocket while receiving the fluid dispensed from the pump device 100.

Still referring to FIG. 1, the controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 4-5, the pump device 100 can be a "one time use" component that is recycled or otherwise discarded after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics, as well as a rechargeable battery) while disposing of the relatively low-cost pump device 100 after each use. Such a pump system 10 can provide enhanced user safety as a new pump device 100' (and drive system therein) is employed with each new fluid cartridge 120'.

The controller device 200 may be equipped with control circuitry 240 (described in connection with FIG. 7) that is programmed to offer a number of feature sets to the user. The different features sets may be implemented, for example, in the user interface components of the controller device 200, in one or more wireless communication components housed in the controller device 200, in one or more sensors housed in the controller device 200, and the like. The controller device 200 can be configured to enable or disable selected feature sets based upon the particular pump device 100 that is removably attached to the controller device 200 to form an electrical connection. In one example as shown in the embodiment in FIG. 1, the controller device 200 can be configured to provide a feature set related to continuous glucose monitoring (CGM) so that the controller device 200 communicate with a wireless glucose sensor device 260. In this example, the controller device 200 may house a wireless communication device 255 that is configured to wirelessly communicate with a communication device 265 of the wireless glucose sensor device 260. The wireless glucose sensor device 260 may include a main body portion that is adhered to a skin surface while a subcutaneous sensor shaft penetrates through the skin to detect the user's blood glucose level. Further, a user interface 220 of the controller device 200 can display the user's glucose level 226 after data from the wireless glucose sensor device 260 is communicated to the controller device 200. In this embodiment, these features related to CGM are automatically enabled in response to the controller device 200 being connected with a first type of pump device 100, and the controller device 200 may automatically disable these features related to CGM if a second type of pump device 100 is attached to the controller device 200. The type of pump device can be defined, for example, by a parameter setting stored in an internal circuit 115 housed in the pump device 100 (e.g., internally stored on an internal memory chip, an identification circuit, or the like). This parameter setting may be a permanent setting that is established by the supplier. Thus, in some embodiments as described in more detail below in connection with FIGS. 9-12, one or more advanced features of controller device 200 may be enabled for the user only when a first type of pump device (e.g., the pump device 100 having a first type of parameter setting) is connected to the controller device 200. In such circumstances, those advanced features of the controller device 200 may be automatically disabled when a second type of pump device (e.g., the pump device 100 having a second type of parameter setting) is connected to the controller device 200.

Still referring to FIG. 1, the pump system 10 can be a medical infusion pump system that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a medicine cartridge 120 in the form of a carpule that is preloaded with medicine suitable for dispensation via a portable infusion system, such as insulin, another medicine for use in the treatment of Diabetes (e.g., Byetta®, Symlin®, or others), a pain relief medicine (e.g., morphine, oxycodone, or the like), an antibiotic medication (e.g., Metronidazole, Penicillin, or the like), a pre-term labor medication, a hormone therapy medication, a blood pressure medication, an anti-emetic medication, an osteoporosis medication, antiviral drugs, anti-inflammatory drugs, antibodies, chemotherapy treatments, anti-cancer drugs (e.g., interferonor or the like), or another injectable medicine. Such a cartridge 120 may be supplied, for example, by Eli Lilly and Co. of Indianapolis, Ind. The fluid cartridge 120 may have other configurations. For example, in some embodiments the fluid cartridge 120 may comprise a reservoir that is fixedly built into the pump housing structure 110.

In some embodiments, the pump device 100 can include one or more structures that interfere with the removal of the medicine cartridge 120 after the medicine cartridge 120 is inserted into the cavity 116. For example, the pump housing structure 110 can include one or more retainer wings (not shown in FIG. 1) that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. Accordingly, the pump device 100 can operate in a tamper-resistant and safe manner because the pump device 100 can be designed with a predetermined life expectancy (e.g., the "one-time-use" feature in which the pump device is discarded after the medicine cartridge 120 is emptied, expired, or otherwise exhausted).

Still referring to FIG. 1, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system 300 (FIG. 8) of the pump device 100. As described in more detail below, the pump device 100 can include a drive system that causes controlled dispensation of the medicine or other fluid from the cartridge 120. In some embodiments, the drive system incrementally advances a piston rod (not shown in FIG. 1) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110. For example, the cap device may include a penetration needle (not shown in FIG. 1) that punctures the septum 121 during attachment of the cap device 130 to the housing structure 110. Thus, when the pump device 100 and the controller device 200 are attached and thereby electrically connected, the controller device 200 communicates electronic control signals via a hardwire-connection (e.g., electrical contacts or the like) to one or more internal components of the pump device 100 so that drive system 300 is urged to dispense medicine from the cartridge 120. Thus, in response to the electrical control signals from the controller device 200, the drive system of the pump device 100 causes medicine to incrementally dispense from the medicine cartridge 120. Power signals, such as signals from the rechargeable battery 245 of the controller device 200 and from the charger battery 345 of the pump device 100 may also be passed between the controller device 200 and the pump device 100.

As shown in FIG. 1, the pump device 100 can include an electrical connector 118 (e.g., having conductive pads, pins, and the like) that is exposed to the controller device 200 and that mates with a complementary electrical connector (refer to connector 218 in FIG. 3) on the adjacent face of the controller device 200. The electrical connectors 118 and 218 provide the electrical communication between the control circuitry 240 (refer, for example, to FIG. 7) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. The electrical connectors 118 and 218 may similarly facilitate transmission of one or more power signals from the rechargeable battery pack 245 to the pump device 100, where the signals may be used to provide power to components of the pump device 100, or to transmit one or more power signals from the charger battery 345 to the controller device, where the signals may be used to recharge the rechargeable battery 245 or to power components of the controller device 200.

Still referring to FIG. 1, the controller device 200 can include the user interface 220 that permits a user to monitor the operation of the pump device 100. In some embodiments, the user interface 220 can include a display device 222 and one or more user-selectable buttons (e.g., several buttons 224 are shown in the embodiment of FIG. 1). The display device 222 can include an active area in which numerals, text, symbols, images, or a combination thereof can be displayed. For example, the display device 222 can be used to communicate a number of settings or menu options for the infusion pump system 10. In this embodiment, the user may press one or more of the buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons of the user interface 220. For example, in embodiments of the infusion pump system 10 configured to dispense insulin, the user may press one or more of the buttons to change the dispensation rate of insulin or to request that a bolus of insulin be dispensed immediately or at a scheduled, later time. In some implementations, the display device 222 may also be used to communicate information regarding remaining battery life, the user's recently detected blood glucose level, and the like.

Accordingly, in some embodiment, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate, wireless control module.

Figure 2:
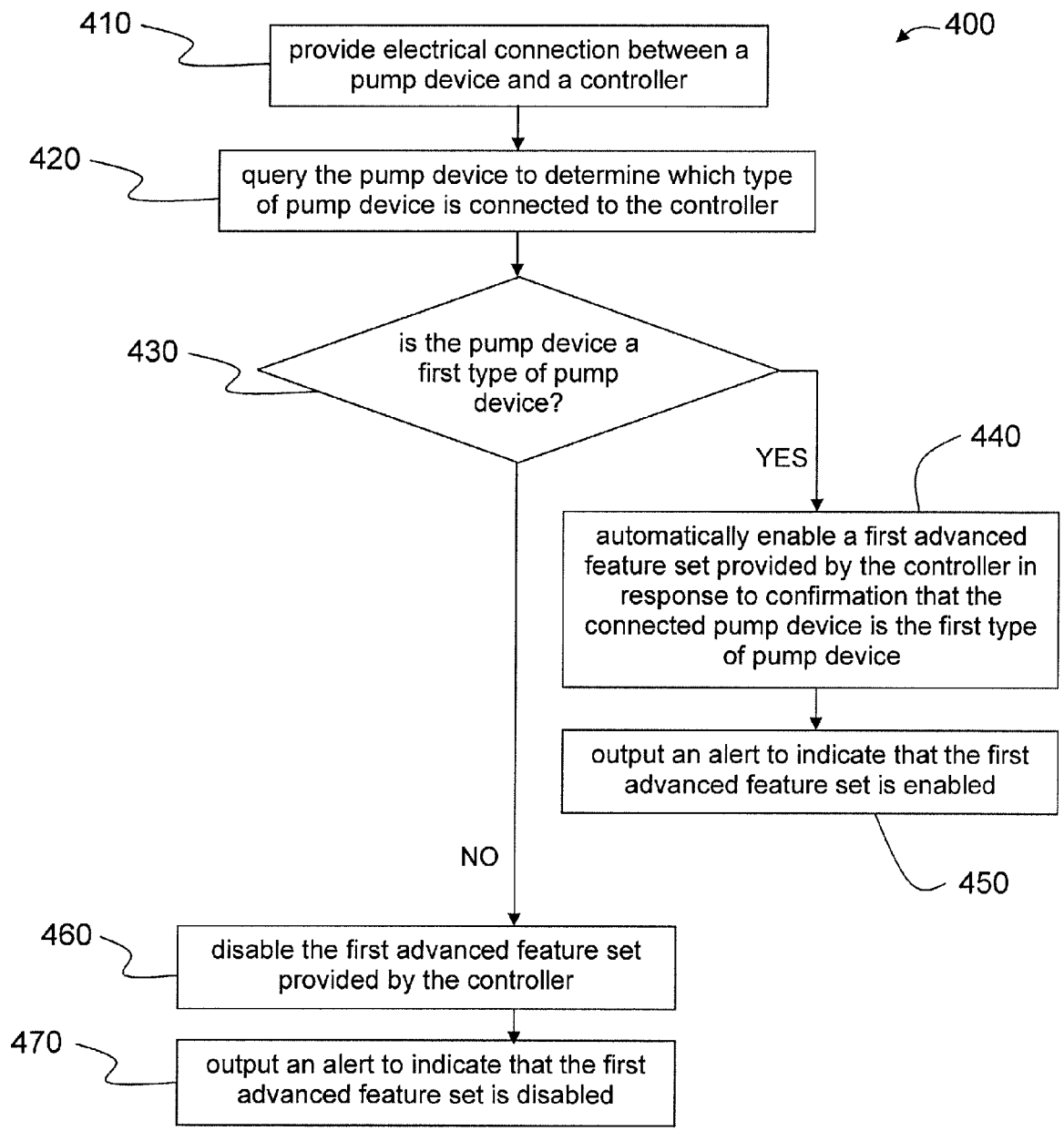
FIG. 2 is a flow chart of a process for using an infusion pump system in accordance with some embodiments.
Figure 3:
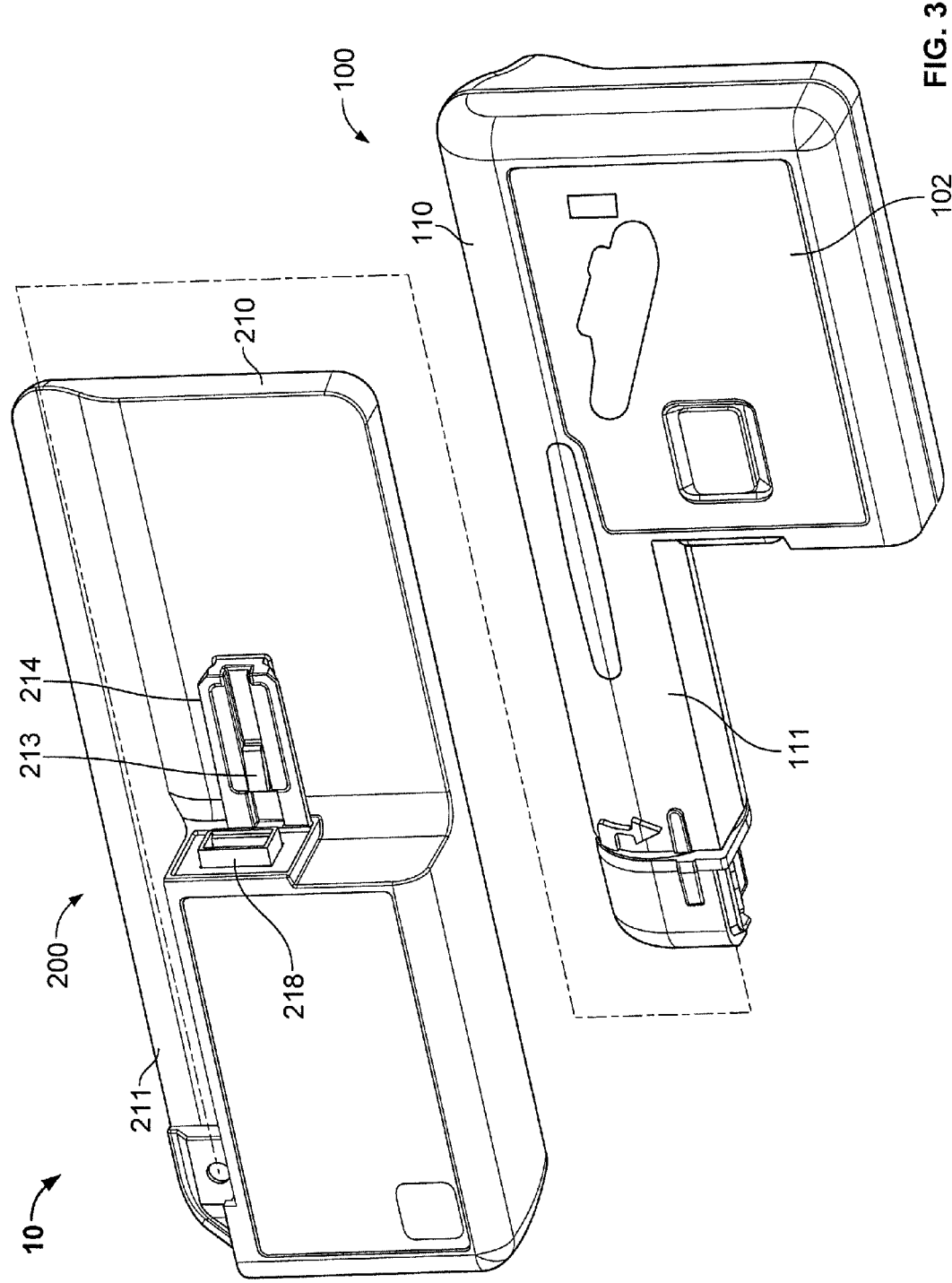
FIG. 3 is a perspective view of the infusion pump system of FIG. 1 in a detached state.

Referring now to FIG. 2, some embodiments of the infusion pump system 10 can be used in a process 400 wherein the controller device 200 enables or disables selected feature sets based upon the particular pump device 100 that is connected to the controller device 200. As previously described, the controller device 200 may be equipped with control circuitry 240 (described in connection with FIG. 7) that is programmed to offer a number of feature sets to the user (e.g., feature sets that facilitate CGM capabilities, capabilities for wireless communication with a blood glucose meter device, training mode capabilities, alternative user interface options depending on medicine to be dispensed, and the like). The different features sets may be implemented, for example, in the user interface components of the controller device 200, in one or more wireless communication components housed in the controller device 200, in one or more sensors housed in the controller device 200, and the like. In this example process 400, the operation 410 can be performed to provide an electrical connection between the pump device 100 and the controller device 200. For example, the electrical connection can be provided when the controller device 200 electrically communicates via the connectors 118 and 218 (FIGS. 1 and 3). In operation 420, the controller device 200 may query the pump device to determine which type of pump device is connected to the controller device 200. For example, as described in more detail below, the pump device 100 may include a parameter setting stored in an internal circuit 115 housed in the pump device 100 (e.g., internally stored on an internal memory chip, an identification circuit, or the like). This parameter setting may be a permanent setting that is established by the supplier. In some embodiments, all of the pump devices 100 are physically similar, and only the parameter setting selected by the supplier defines which type of pump device will be communicated to the controller device 200.

If the controller device 200 determines in operation 430 that the connected pump device 100 is a first type of pump device 100 (e.g., a parameter setting of "1"), the process 400 continues to operation 440. In operation 440, the controller device 200 may automatically (e.g., without manual intervention by the user) enable a first advanced feature set provided by the controller device 200. For example, if the controller device 200 is programmed to provide CGM capabilities, the controller device 200 may automatically activate the wireless communication device 255 (FIG. 1) and activate the "Glucose Level" output 226 (FIG. 1) on the user interface display 222. In operation 450, the controller device 200 can output an alert indicative that the first advanced feature set is enabled. For example, the alert message 225 (FIG. 1) can be output to notify the user of the activation of the advanced capabilities.

Still referring to FIG. 2, if the controller device 200 determines in operation 430 that the connected pump device 100 is not a first type of pump device 100 (e.g., a parameter setting different than "1"), the process 400 continues to operation 460. In operation 460, the controller device 200 may automatically (e.g., without manual intervention by the user) disable the first advanced feature set provided by the controller device 200. For example, if the controller device 200 is programmed to provide CGM capabilities, the controller device 200 may disable the wireless communication device 255 (FIG. 1) and prevent display of the "Glucose Level" output 226 (FIG. 1). In doing so, the battery life of the controller device 200 may be extended because the advanced components are not activated to draw power from the battery. In operation 470, the controller device 200 can output an alert indicative that the first advanced feature set is disabled. For example, the controller device 200 may display an alert message to notify the user of that the advanced capabilities and not activated until a different type of pump is connected to the controller device 200. Thus, the process 400 may be implemented so that one or more advanced features of controller device 200 are enabled for the user when a first type of pump device (e.g., the pump device 100 having a first type of parameter setting) is connected to the controller device 200. Also, those advanced features of the controller device 200 may be automatically disabled when a second type of pump device (e.g., the pump device 100 having a second type of parameter setting) is connected to the controller device 200.

Referring now to FIG. 3, the controller device 200 can be removably attached to the pump device 100 during operation of the infusion pump system 10 to dispense medicine. For example, the pump device 100 may be moved in a longitudinal direction toward the controller device 200 until the complementary features connect and secure the separate components in the side-by-side arrangement. Moreover, in some embodiments, the pump device 100 and controller device 200 can be readily attached together with a "one-movement" process that is convenient to the user.

The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. Also, the pump housing 110 may include a protrusion 113 that mates with a spring-biased latch 213 of the controller housing 210, and the pump housing 110 may further include grooves 114 that mate with a tongue structure 214 of the controller housing 110 so as to provide longitudinal guided motion during the attachment process. In various implementations, the pump device 100 and the controller device 200 can be mounted to one another so that the assembled system 10 is resistant to water migration both into the pump housing structure 110 and the controller housing structure 210. For example, a gasket seal around the electrical connector 118 can provide water-resistant protection for the electrical connection between the pump device 100 and the controller device 200. Thus, the sensitive internal components in the controller device 200 and the pump device 100 can be reliably protected from water migration if the user encounters water (e.g., rain, incidental splashing, and the like) while using the pump system 10.

Figure 4:
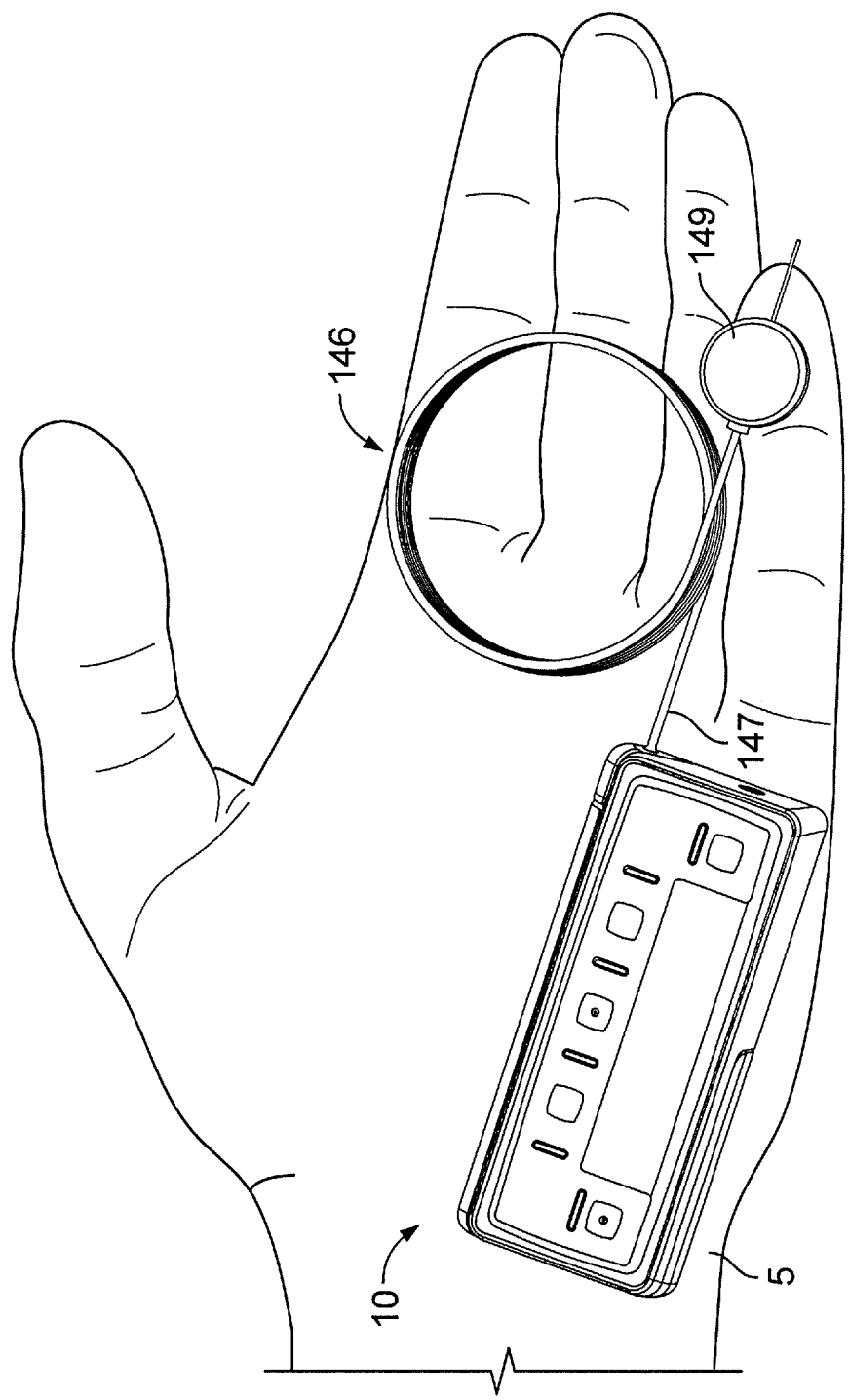
FIG. 4 is a perspective view of the infusion pump system of FIG. 1 in an attached state.

Referring to FIG. 4, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The pump system 10 is shown in FIG. 4 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the patient so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

In some embodiments, the infusion pump system 10 can be pocket-sized so that the pump device 100 and controller device 200 can be worn in the user's pocket or in another portion of the user's clothing. In some circumstances, the user may desire to wear the pump system 10 in a more discrete manner. Accordingly, the user can pass the tube 147 from the pocket, under the user's clothing, and to the infusion site where the adhesive patch can be positioned. As such, the pump system 10 can be used to deliver medicine to the tissues or vasculature of the user in a portable, concealable, and discrete manner.

In some alternative embodiments, the infusion pump system 10 can be configured to adhere to the user's skin directly at the location in which the skin is penetrated for medicine infusion. For example, a rear surface 102 (FIG. 3) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Figure 5:
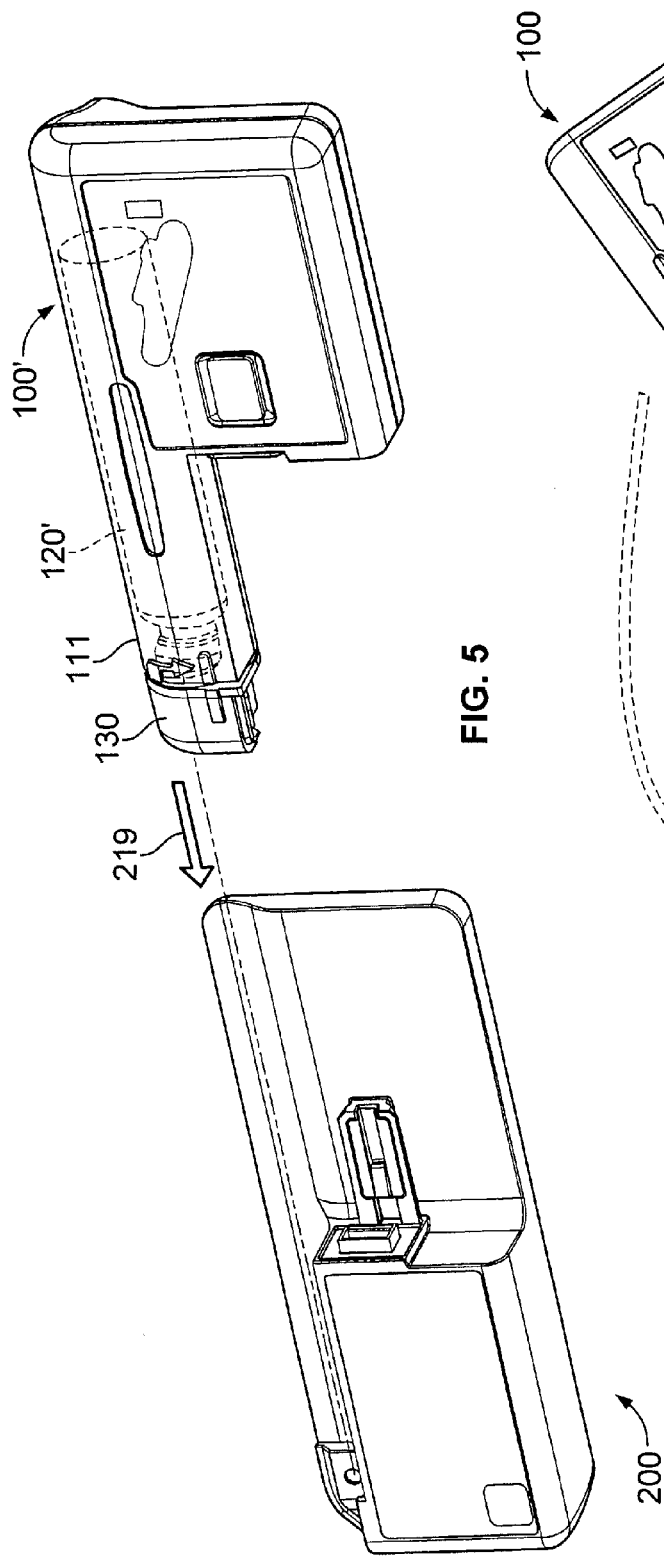
FIGS. 5-6 are perspective views of the pump device of FIGS. 1 and 3 being discarded and the controller device of FIGS. 1 and 3 being reused with a new pump device.
Figure 6:
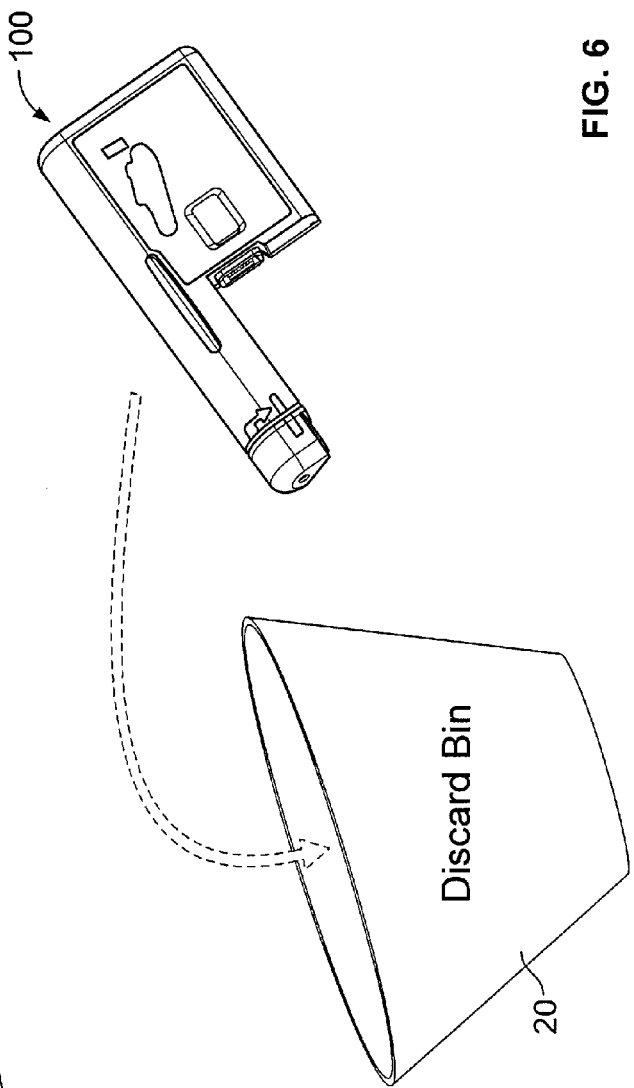

Referring now to FIGS. 5-6, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, a medicine cartridge 120 containing insulin can have an expected usage life of about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, the rechargeable battery pack 245, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics, and a rechargeable battery pack) while disposing of the relatively low-cost pump device 100 after each use. Such a pump system 10 can provide enhanced user safety as a new pump device 100' (and drive system therein) is employed with each new fluid cartridge 120'.

Referring to FIGS. 5-6, the same controller device 200 can be reused with a new pump device 100' having a new medicine cartridge 120' retained therein, and the previously used pump device 100, including the exhausted medicine cartridge, can be discarded in a discard bin 20. The new pump device 100' (FIG. 4) can have a similar appearance, form factor, and operation as the previously used pump device 100, and thus the new pump device 100' can be readily attached to the controller device 200 for controlled dispensation of medicine from the new medicine cartridge 120'. Each time a new pump device 100' is connected to the controller device 200, the controller device 200 may query the pump device 100 to determine which type of pump is being connected (as described, for example, in the process 400 of FIG. 2). In some embodiments, the user can prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 4, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the infusion set patch to the user's skin. As shown in FIG. 4, the new medicine cartridge 120' may be filled with medicine such that the plunger 125 is not viewable through the barrel 111.

The new pump device 100' can be removably attached to the controller device 200 to assemble into the infusion pump system 10 for delivery of medicine to the user. As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction 219) that causes both a physical connection and an electrical connection. Thus, the infusion pump system 10 can permit users to readily join the pump device 100' and the controller device 200 without compound or otherwise difficult hand movements—a feature that can be beneficial to child users or to elderly users.

Figure 7:
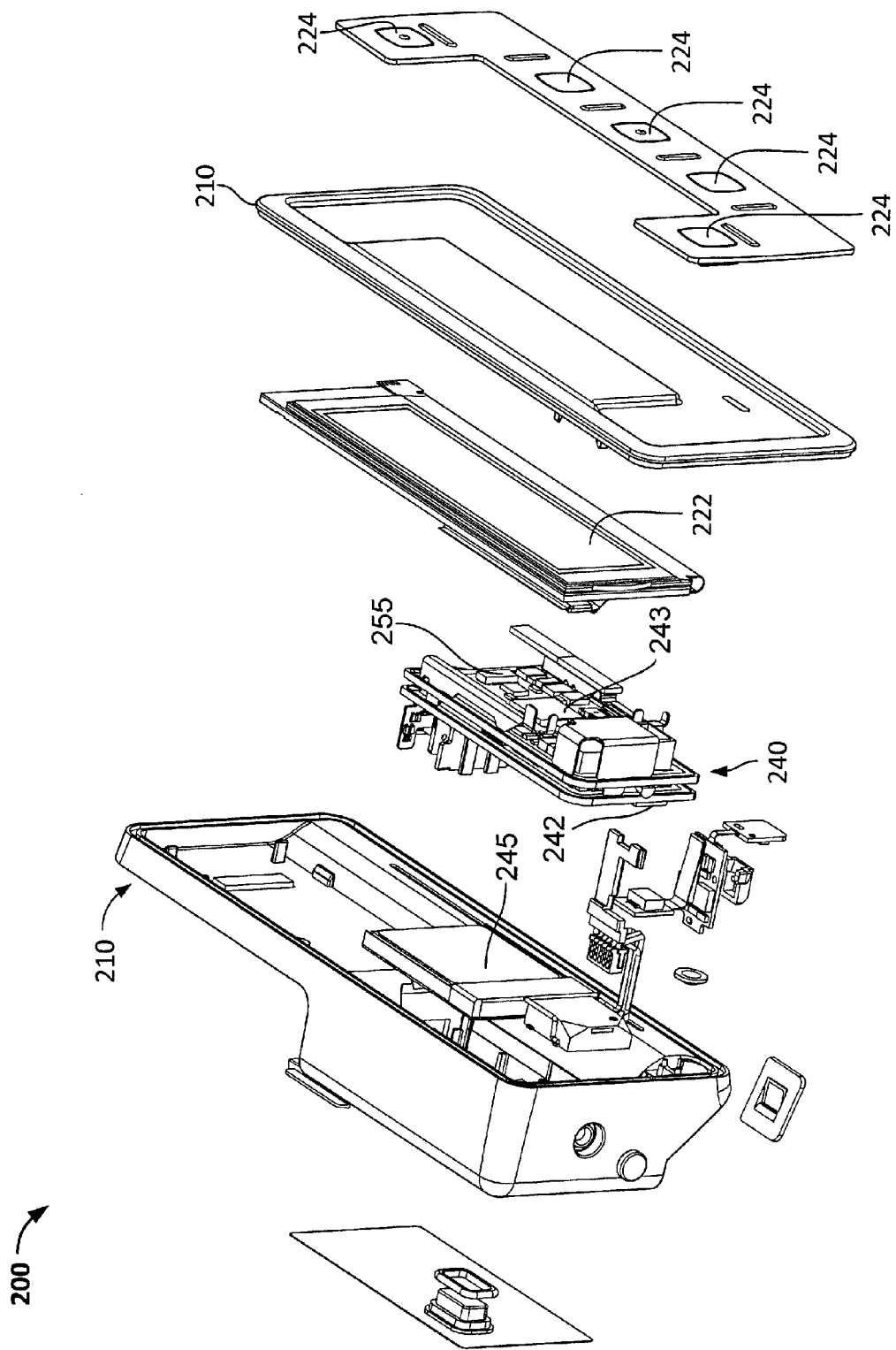
FIG. 7 is an exploded perspective view of a controller device for an infusion pump system, in accordance with some embodiments.

Referring now to FIG. 7, the controller device 200 (shown in an exploded view) houses a number of components that can be reused with a series of successive pump devices 100. In particular, the controller device 200 can include control circuitry 240 and rechargeable battery pack 245, each arranged in the controller housing 210. As described above, rechargeable battery pack 245 may provide electrical energy to components of control circuitry 240, other components of the controller device (e.g., a display device 222 and other user interface components, sensors, or the like), or components of the pump device 100. Controller circuitry 240 may be configured to communicate control signals to components of the pump device 100 (e.g., so as to activate the drive system), or to receive power or feedback signals from the pump device 100. In some embodiments, the control circuitry 240 can be implemented as one or more printed circuit boards having a number of electronic components mounted thereto. It should be understood that although the control circuitry 240 is depicted as comprising one or more printed circuit boards, the control circuitry 240 can have other forms, including a flexible circuit substrate and other configurations.

Still referring to FIG. 7, the user interface 220 of the controller device 200 can include input components and/or output components that are electrically connected to the control circuitry 240. For example, the user interface 220 can include the display device 222 having an active area that outputs information to a user and buttons 224 that the user can use to provide input. Here, the display device 222 can be used to communicate a number of settings or menu options for the infusion pump system 10. In some embodiments, the controller circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). As previously described, the control circuitry 240 can be programmable by user to change any one of a number of settings for the infusion pump system 10. For example, the user may provide one or more instructions to adjust a number of basal dosage settings or bolus options for the operation of the infusion pump system 10. Such settings may be stored in the memory devices arranged in the controller circuitry 240. The controller circuitry 240 can include other components, such as sensors, that are electrically connected to the circuit board.

Some embodiments of the controller circuitry 240 can include a cable connector (e.g., a USB connection port or another data cable port) that is accessible on an external portion of the controller housing 210. As such, a cable can be connected to the controller circuitry 240 to upload data or program settings to the controller circuitry 240 or to download data from the controller circuitry 240. For example, historical data of medicine delivery can be downloaded from the controller circuitry 240 (via the cable connector) to a computer system of a physician or a user for purposes of analysis and program adjustments. Optionally, the data cable can also provide recharging power.

Still referring to FIG. 7, a perspective view of portions of controller circuitry 240 and the rechargeable battery pack 245 is shown. Rechargeable battery pack 245 may include one or more lithium-ion or lithium-polymer battery cells, and the rechargeable battery pack 245 can be coupled to one or the circuit boards housed in the controller device 200. In some implementations, the lithium-ion or lithium-polymer battery 500 may be a 3.8 volt battery. The rechargeable battery pack 245 can include a high-current-output battery that is capable of discharging a brief current burst to power, for example, the drive system 300 of the pump device 100, and can also provide energy sources for various electronic components of the infusion pump system 10. Alternative embodiments of the rechargeable battery 245 can include a combination of batteries and capacitors. The rechargeable battery 245 may be capable of accepting and storing electrical energy over time (e.g., "trickle charge"). For example, the rechargeable battery 245 can be charged with energy supplied from a pump power source 345 (FIG. 8), according to some implementations. The rechargeable battery 245 can receive electrical energy from the pump power source 345 housed in the pump device 100 (e.g., the charger battery 345), from a plug-in wall charger, from a cable connector (e.g., a USB connection port that is connected to the controller circuitry 240), or from another charging device (e.g., a charging cradle), according to some implementations.

Accordingly, the infusion pump system 10 can include two power sources 345 and 245—one arranged in the disposable pump device 100 and another arranged in the reusable controller device 200—which can permit a user to continually operate the controller device 200 without having to recharge a battery via a plug-in wall charger or other cable. Because the controller device 200 can be reusable with a number of pump devices 100 (e.g., attach the new pump device 100' after the previous pump device 100 is expended and disposed), the rechargeable battery 245 in the controller device can be recharged over a period of time, each time when a new pump device 100' is connected thereto. Such a configuration can be advantageous in those embodiments where the pump device 100 is configured to be a disposable, one-time-use device that attaches to a reusable controller device 200. For example, in those embodiments, the "disposable" pump devices 100 recharges the rechargeable battery 245 in the "reusable" controller device 200, thereby reducing or possibly eliminating the need for separate recharging of the controller device 200 via a power cord plugged into a wall outlet.

Still referring to FIG. 7, a main processor 242 can be mounted to one of the circuit boards of the control circuitry 240 housed in the controller device 200. In various implementations, processor 242 may comprise one or more microprocessors, microcontrollers, digital signal processors, instantiated cores within one or more programmable logic devices (e.g., application specific integrated circuit, field programmable gate array, complex programmable logic device), or the like. Processor 242 may execute instructions and perform tasks associated with the infusion pump system. For example, the processor 242 may coordinate the electrical communication to and/or from the controller device 200 (e.g., communication between the controller device 200 and the pump device 100). Processor 242 may receive inputs indicative of various statuses relating to the infusion pump system. For example, the processor 242 may receive one or more inputs that indicate the type of pump device that is connected to the controller device 200, the activated/deactivated status of the wireless communication device 255, the charge status of the rechargeable battery 245, or the like.

In various implementations, processor 242 executes instructions stored in memory locations internal of the processor 242 or in memory locations in one or more memory devices external of the processor 242. For example, in some embodiments the processor 242 may include on-board random access memory (RAM), where instructions may be loaded and executed therefrom by the processor 242. Processor 242 may also include various forms of on-board non-volatile memory for storing instructions or data in some implementations, including but not limited to EPROM, EEPROM, Flash, and the like. In some embodiments, memory devices external of the processor 242 are used. A memory device 243 may store instructions, data, or both, for use by the processor 242. In some implementations, memory device includes FRAM data storage. Memory device 242 may store user settings and alarms, as well as parameters for the infusion pump system 10, including last-used pump parameters. It should be understood from the description herein that the circuit board configuration of the control circuitry 240 can be selected so as to modify the location of the processor 242, memory devices 243, rechargeable battery 245, and the wireless communication device 255 within the controller housing 210.

Figure 8:
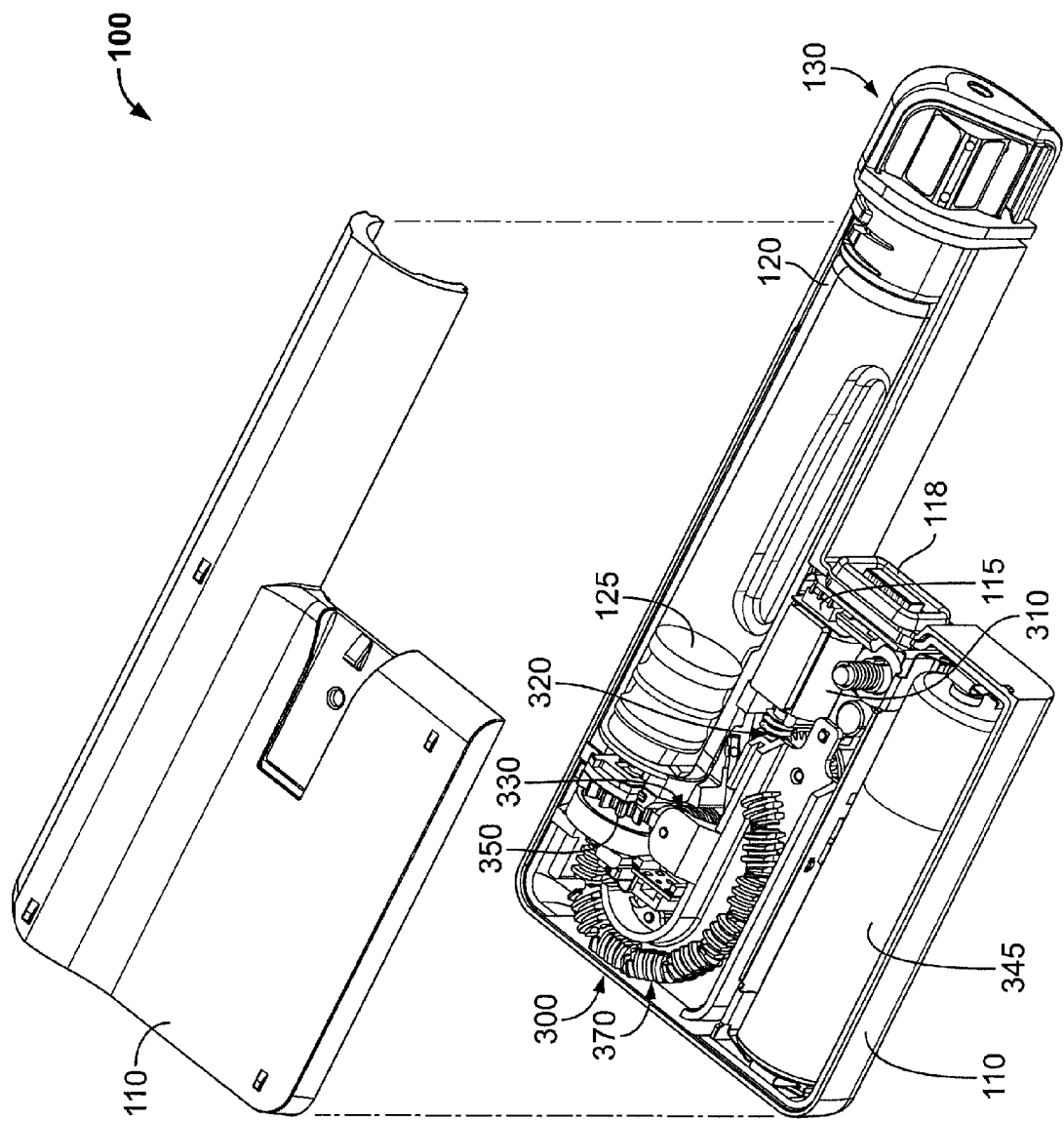
FIG. 8 is an exploded perspective view of a pump device for an infusion pump system, in accordance with some embodiments.

Referring now to FIG. 8, in some embodiments, the pump device 100 can include a power source 345, referred to above as a charger battery. In some embodiments, the power source 345 is an alkaline battery cell, such as a 1.5 Volt "AAA" alkaline battery cell. The power source 345 may be capable of transmitting electrical energy to the controller device 200 when the pump device 100 is attached to the controller device 200, via connectors 118 and 218 as described above. For example, the power source 345 may be used to recharge the rechargeable battery pack 245 when the pump device 100 is attached to the controller device 200. In some embodiments, the power source 345 is used to provide energy to the drive system 300 of the pump device 100, and also to electronic components of the controller device 200. In some circumstances, the power source 345 may provide the energy to power all aspects of the infusion pump system 10. In some circumstances, the rechargeable battery 245 may provide the energy to power all aspects of the infusion pump system 10. In some circumstances, the rechargeable battery 245 and the power source 345 (charger battery) may each be responsible for powering particular aspects of the infusion pump system 10. In some circumstances, the rechargeable battery 245 may provide the energy to supplement the energy provided by the power source 345 to power aspects of the infusion pump system.

The pump device 100 can include the drive system 300 that is controlled by the controller device 200. The drive system 300 can accurately and incrementally dispense fluid from the pump device 100 in a controlled manner. In this embodiment, the drive system 300 includes an electrically powered actuator 310 (e.g., a rotational motor), a gear system 320, a ratchet mechanism 330 that incrementally rotates a gear wheel 350, and a threaded piston rod 370 that is urged toward to the plunger 125 of the medicine cartridge 120. The pump device 100 can include a connector circuit to facilitate the transfer of signals to and from the electrical connector 118. In some implementations, the connector circuit in the pump device 100 can include internal circuit 115 (e.g., an internal memory chip, an identification circuit, or the like). The internal circuit 115 can be used to store the parameter setting that defines which type of pump device will be communicated to the controller device 200. This parameter setting may be a permanent setting that is established by the supplier. The internal circuit 115 may also store data regarding the pump device 100 and its operational history. As previously described, the electrical connector 118 of the pump device 100 can mate with the connector 218 (FIG. 2) of the controller device 200 so that electrical communication can occur between the pump device 100 and the controller device 200. In some embodiments, the connection can operate as a passageway for the control signals (from the controller circuitry 240 of the controller device 200) transmitted to the drive system 300 or other components of the pump device 100.

Figure 9:
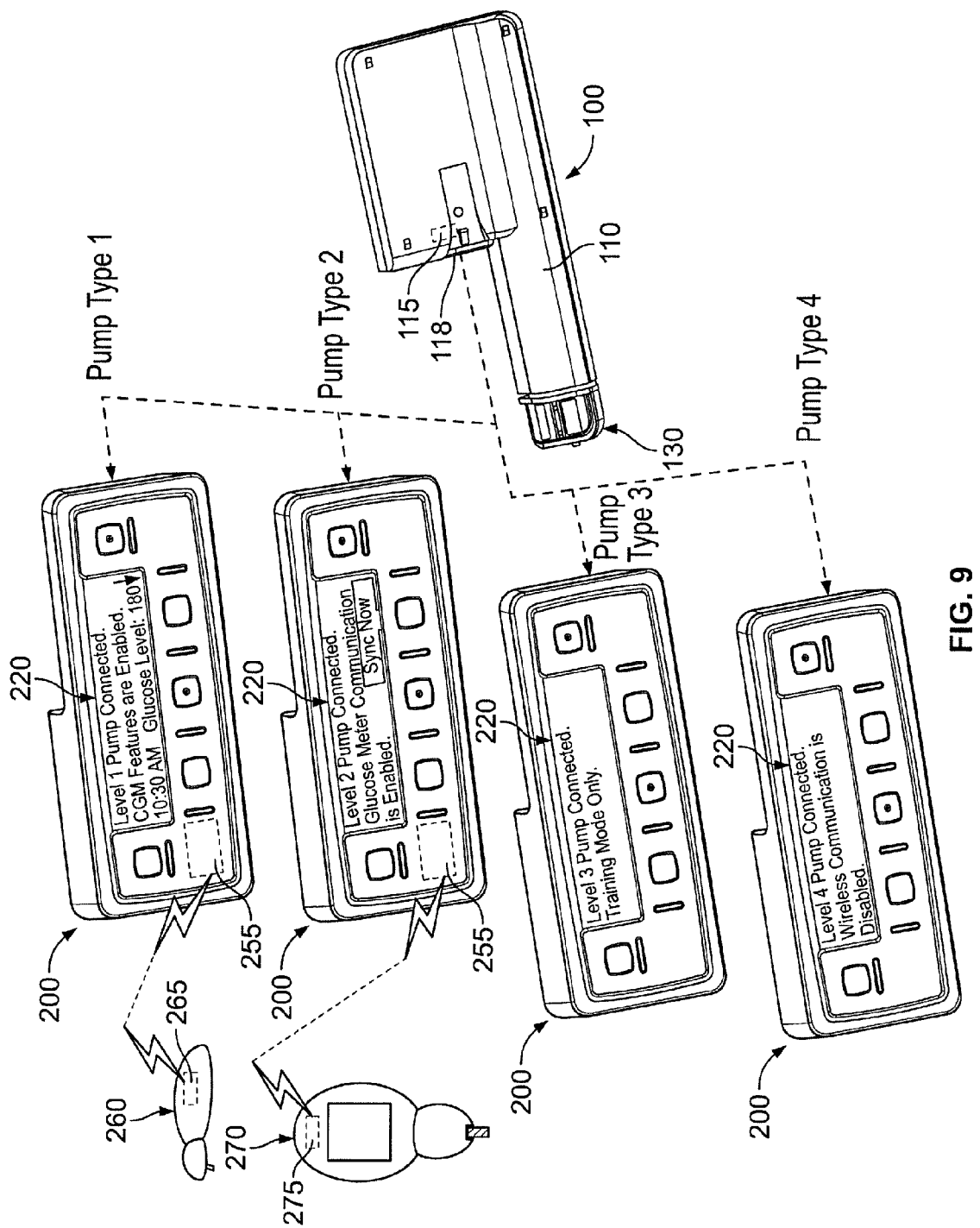
FIG. 9 is an exploded perspective view of an infusion pump system including a controller device that provides different feature sets in response to connection with a particular type of pump device, in accordance with some embodiments.

Referring now to FIG. 9, some embodiments of the controller device 200 can be configured to automatically enable or disable particular features to be provided by the controller in response to a connection with a particular type of pump device 100. As previously described, the controller device 200 in this embodiment is equipped with the control circuitry 240 that is programmed to offer a number of different feature sets to the user. The different features sets may be implemented, for example, in the user interface 220 of the controller device 200, in one or more wireless communication components 255 housed in the controller device 200, in one or more sensors or electronic components housed in the controller device 200, or a combination thereof. Thus, each controller device 200 can be configured to connect with several different types of pump devices 100. The particular type of pump device 100 can be defined by an electronic indicator, for example, a parameter setting stored in the internal circuit 115 housed in the pump device 100 (e.g., internally stored on an internal memory chip, an identification circuit, or the like). This parameter setting may be a permanent setting that is established by the supplier. In particular embodiments, the different types of pump devices 100 can have substantially the same shape, size, and mechanical configuration, so the different types of pump devices 100 are different from one another only in the parameter setting stored in the internal circuit 115.

It should be understood from the description herein that the electronic indicator that is used to at least partially define the type of pump device may have a form other than the parameter setting stored in the internal circuit 115. For example, in alternative embodiments, the particular type of pump device 100 can be defined by connecting a series of pins of the electrical connector 118 to different voltage levels (Low or high). In such embodiments, the electrical connector 118 of the pump device 100 can include three designated connector pins to define eight (2×2×2=8) different types of the pump devices that are readily recognized by the controller device 200 when the controller connector 218 mates with the pump connector 118. In a second example of an alternative embodiment, the particular type of pump device 100 can be defined by a resistor value in a circuit coupled to the electrical connector 118 of the pump body. For instance, the resistor value of a particular resistor (or series of resistors) mounted in the pump device 100 can cause a switch of the control circuitry 240 to be shifted to a "closed" state or "open" state in response to the controller connector 218 connecting with the pump connector 118. In a third example of an alternative embodiment, the particular type of pump device 100 can be defined by the absence or presence of a light reflecting surface within the pump device 100. For example, the controller device 200 can be equipped with a light emitter and light receiver that are positioned adjacent to the pump device 100 when the pump device 100 and controller device 200 are removably attached. As such, the light emitter can emit a light beam that is reflected from the light reflecting surface of a first type of pump device 100 and returns to the light receiver, thereby allowing the controller to recognize that the first type of pump device 100 is attached to the controller device 200. Conversely, the light emitter can emit a light beam that is not reflected from the second type of pump device (which is lacking the light reflecting surface) so that little or no light returns to the light receiver, thereby allowing the controller to recognize that the second type of pump device 100 is attached to the controller device 200. In a fourth example of an alternative embodiment, the particular type of pump device 100 can be defined by the absence or presence of a magnet housed in the pump housing 110 at a predetermined position. In such embodiments, the controller device 200 can be equipped with a magnetic sensor (e.g., a Hall effect sensor, an induction coil, or the like) that indicates whether the pump device 100 is a first type (having the magnet housed therein) or a second type (not having the magnet housed therein). In a fifth example of an alternative embodiment, the particular type of pump device 100 can be defined by the presence or absence (or a particular type) of an RFID (radio frequency identification) chip housed in the pump housing 110 at a predetermined position. In such embodiments, the controller device 200 can be equipped with an RFID sensor that detects the presence or absence (or the particular type) of the RFID chip of the pump device 100. The RFID sensor can be coupled to the control circuitry 240 so as to indicates which type of pump device 100 is connected to the controller device 200.

Still referring to FIG. 9, some embodiments of the controller device 200 can be configured to provide a first feature set related to CGM, a second feature set related to wireless communication with a blood glucose meter (e.g., a blood test strip reader), a third feature set related to training mode options (e.g., for new users), and a basic feature set to provide basal and bolus infusion options. Some or all of these feature sets can be automatically enabled or disabled by the controller device 200 in response to a connection with a particular type of pump device. In one example, if the pump device 100 is a first type of pump (e.g., a parameter setting of pump type "1"), the controller device 200 is configured to automatically activate the feature set related to CGM in response to the controller device 200 being connected with the first type of pump device 100. In such circumstances, the controller device 200 may activate the wireless communication device 255 that is configured to wirelessly communicate with the communication device 265 of the wireless glucose sensor device 260. Further, the user interface 220 of the controller device 200 can continuously display the user's glucose level 226 after data from the wireless glucose sensor device 260 is communicated to the controller device 200. Also, the user interface 220 of the controller device 200 may display CGM menu options and may output an alert to notify the user that the advanced features are now enabled. Optionally, the controller device 200 may also enable wireless communication with blood glucose meter 270 (described below) in response to a connection with the first type of pump device 100. In such circumstances, the first type of pump device 100 may be referred to as an advanced pump device that triggers the activation of some or all of the advanced feature sets provided by the controller device 200.

In a second example, if the pump device 100 is a second type of pump (e.g., a parameter setting of pump type "2"), the controller device 200 is configured to automatically activate the feature set related to wireless communication with the blood glucose meter 270 in response to the controller device 200 being connected with the second type of pump device 100. In such circumstances, the controller device 200 may activate the wireless communication device 255 that is configured to wirelessly communicate with the wireless communication device 275 of the glucose meter 270. Further, the user interface 220 of the controller device 200 can display a prompt for the user to synchronized with the glucose meter 270 ("Sync Now" option), which then leads the user to calculate a bolus in response to receiving the wireless data from the glucose meter 270. Also, the user interface 220 of the controller device 200 may display glucose meter menu options and may output an alert to notify the user that the glucose meter communication feature are now enabled. In particular embodiments, the user interface 220 of the controller device 200 may output an alert to notify the user that the features related to CGM will be disabled until a first type of pump is connected with the controller. The controller device 200 may automatically disable the features related to CGM when a second type of pump device 100 is connected thereto so as to conserve the controller resources and battery power.

In a third example, if the pump device 100 is a third type of pump (e.g., a parameter setting of pump type "3"), the controller device 200 is configured to automatically activate the feature set related to a training mode in response to the controller device 200 being connected with the third type of pump device 100. In such circumstances, the controller device 200 may activate the user interface to provide simplified or reduced menu options to the user. For example, when the controller device 200 enables the training mode feature set, the dosage options available to the user via the user interface 220 may be limited to a selected subset of basal profiles (e.g., a basic basal delivery profile with three time segments in a 24-hour period) and may be limited to basic bolus options (e.g., single meal bolus profiles without options for a timed bolus or a combo bolus). As such, the training mode feature set can assist a new user in learning to operate the pump system 10 without inadvertently selecting complex medicine delivery options. In some embodiments, when the controller device 200 enables the training mode feature set, the pump device 100 may dispense the medicine in accordance with the selected basal and bolus delivery options. In alternative embodiments, when the controller device 200 enables the training mode feature set, the controller device 200 may disable pump drive control signals to the pump device 100 so that no medicine is dispensed (because the drive system is not advanced forward). In such embodiments, the training mode feature set would be understood as an early training tool before the user elects to begin pumping. In the wireless communication device 255 that is configured to wirelessly communicate with the wireless communication device 275 of the glucose meter 270. The user interface 220 of the controller device 200 may output an alert to notify the user that the training mode feature set is now enabled in response to connection with the third type of pump device 100. In particular embodiments, the user interface 220 of the controller device 200 may output an alert to notify the user that other advanced features (e.g., features related to CGM, features related to wireless communication with a glucose meter, features related to advanced basal and bolus options, and the like) will be disabled until a different type of pump is connected with the controller device 200.

In a fourth example, if the pump device 100 is a fourth type of pump (e.g., a parameter setting of pump type "4"), the controller device 200 is configured to automatically activate the feature set related to basic pumping operations in response to the controller device 200 being connected with the fourth type of pump device 100. In such circumstances, the controller device 200 may activate the user interface 220 to provide a full set of basal and bolus delivery options while more advanced features (e.g., features related to CGM, features related to wireless communication with a glucose meter, and the like) are disabled. The user interface 220 of the controller device 200 may output an alert to notify the user that the basic pumping features are now enabled. In particular embodiments, the user interface 220 of the controller device 200 may output an alert to notify the user that the advanced features (e.g., features related to CGM, features related to wireless communication with a glucose meter, and the like) will be disabled until a first type of pump is connected with the controller. The controller device 200 may automatically disable the features related to wireless communication when a fourth type of pump device 100 is connected thereto so as to conserve the controller resources and battery power.

Figure 10:
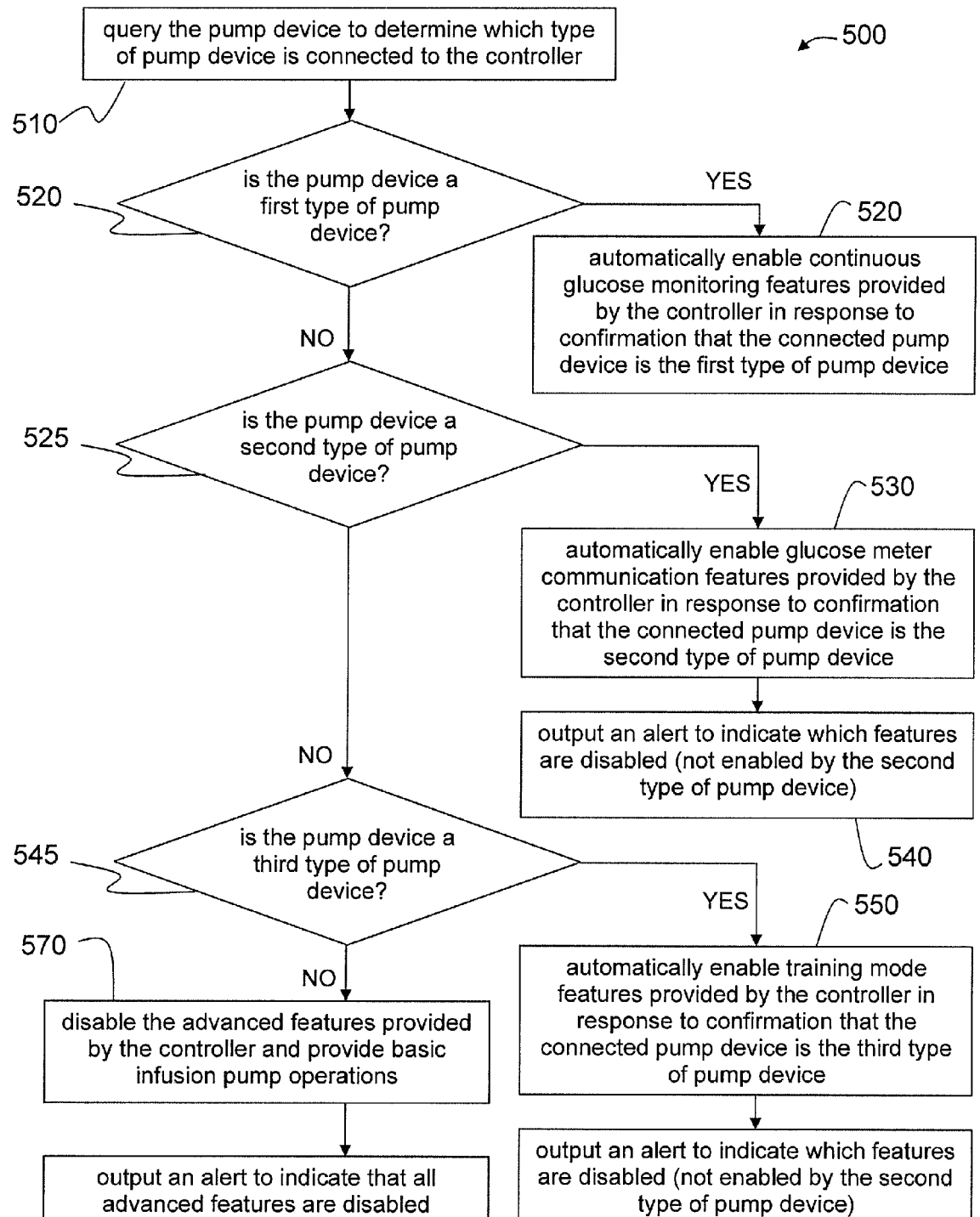
FIG. 10 is a flow chart of a process for using the infusion pump system of FIG. 9, in accordance with some embodiments.

Referring now to FIG. 10, some embodiments of the infusion pump system 10 can be used in a process 500 wherein the controller device 200 is configured to connect with three or more different types of pump devices 110. For example, as described in connection with FIG. 9, the controller device 200 can enable or disable selected feature sets in response to a connection with any one of four different types of pump device 100. In this process 500, the controller device 200 may be equipped with control circuitry 240 (described in connection with FIG. 7) that is programmed to offer a number of feature sets to the user, and the different features sets may be implemented, for example, in the user interface components of the controller device 200, in one or more wireless communication components housed in the controller device 200, in one or more sensors or electronic components housed in the controller device 200, and the like. In this example process 500, the operation 510 can be performed to by the controller device 200 to query the pump device 100 to determine which type of pump device is connected to the controller device 200. For example, as previously described in connection with FIG. 9, the pump device 100 may include an electronic indicator (e.g., a parameter setting stored in an internal circuit 115 housed in the pump device 100) that is detected by the control circuitry 240 in response to connection between the pump device 100 and the controller device 200.

If the controller device 200 determines in operation 515 that the connected pump device 100 is a first type of pump device 100 (e.g., a parameter setting of "1"), the process 500 continues to operation 520. In operation 520, the controller device 200 may automatically (e.g., without manual intervention by the user) enable a first advanced feature set related to CGM capabilities. For example, the controller device 200 may automatically activate the wireless communication device 255 (FIG. 1) and activate the "Glucose Level" output 226 (FIG. 1) on the user interface display 222. As previously described, the controller device 200 may optionally output an alert indicative that this advanced feature set related to CGM is enabled.

Still referring to FIG. 10, if the controller device 200 determines in operation 525 that the connected pump device 100 is a second type of pump device 100 (e.g., a parameter setting of "2"), the process 500 continues to operation 530. In operation 530, the controller device 200 may automatically enable a second advanced feature set related to wireless communication with a glucose meter 270 (FIG. 9). For example, the controller device 200 may automatically activate the wireless communication device 255 (FIG. 1) and activate the user interface display 222 to provide a prompt to the user (FIG. 9). The controller device 200 may optionally output an alert indicative that this feature set related to communication with the glucose meter 270 is enabled. Also, in operation 540, the controller device 200 can output an alert indicative of which features are disabled (e.g., features related to CGM).

If the controller device 200 determines in operation 545 that the connected pump device 100 is a third type of pump device 100 (e.g., a parameter setting of "3"), the process 500 continues to operation 550. In operation 550, the controller device 200 may automatically enable a third feature set related to training mode options (FIG. 9). For example, the controller device 200 may automatically change the user interface so that the dosage options available to the user via the user interface 220 are limited to a selected subset of basal profiles (e.g., a basic basal delivery profile with three time segments in a 24-hour period) and are also limited to basic bolus options (e.g., single meal bolus profiles without options for a timed bolus or a combo bolus). The controller device 200 may optionally output an alert indicative that the training mode feature set is enabled. Also, in operation 560, the controller device 200 can output an alert indicative of which features are disabled (e.g., features related to CGM, features related to wireless communication with a glucose meter, features related to advanced basal and bolus options, and the like).

If the controller device 200 determines in operation 545 that the connected pump device 100 is not a first, second, or third type of pump device 100 (e.g., a fourth type of pump device having a parameter setting of "4"), the process 500 continues to operation 570. In operation 570, the controller device 200 may automatically enable the user interface 220 to provide a full set of basal and bolus delivery options while more advanced features (e.g., features related to CGM, features related to wireless communication with a glucose meter, and the like) are disabled. The controller device 200 may optionally output an alert indicative that the basic pumping features are enabled. Also, in operation 580, the controller device 200 can output an alert indicative that all of the advanced feature sets are disabled.

Figure 11:
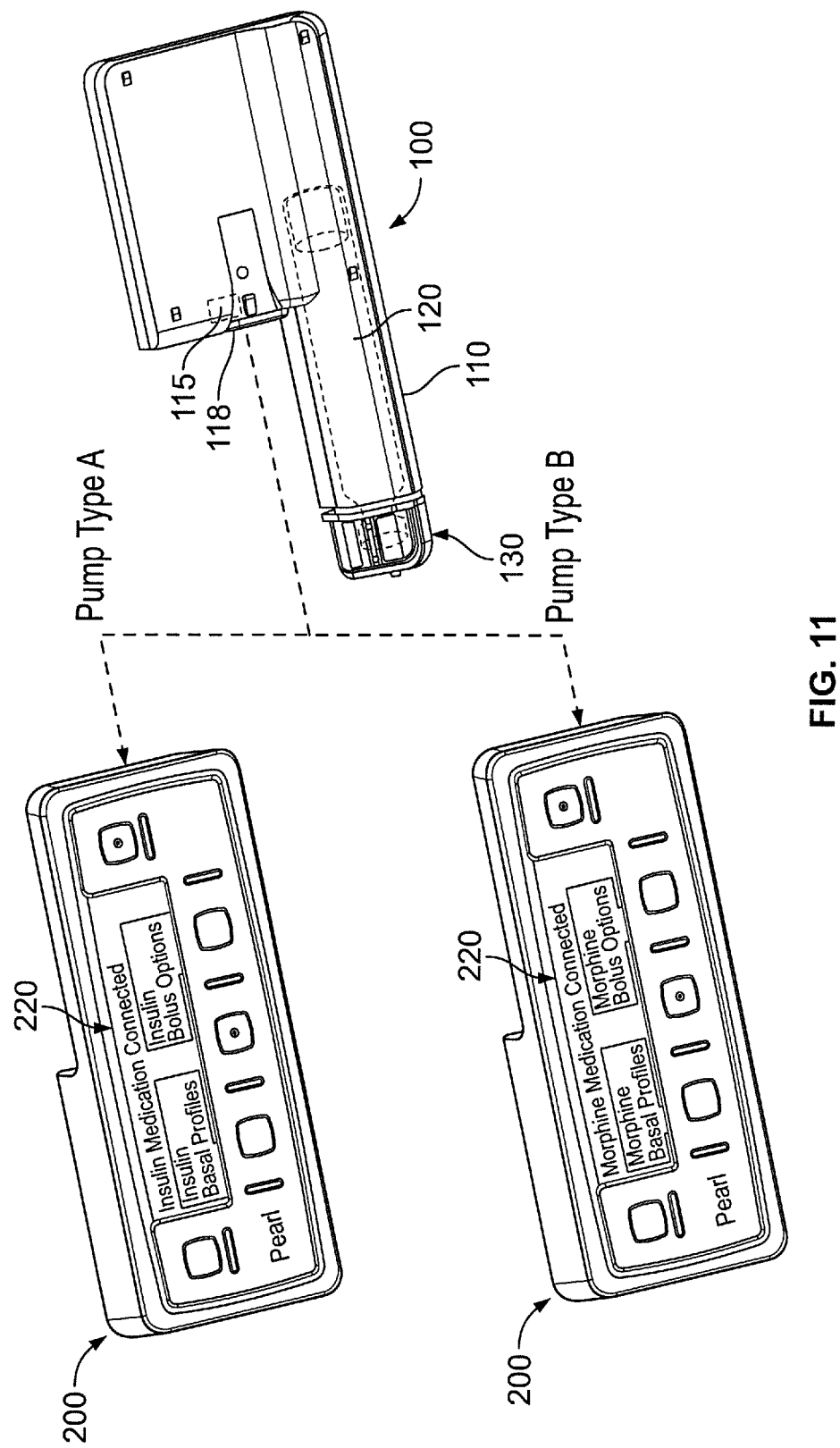
FIG. 11 is an exploded perspective view of an infusion pump system including a controller device that provides different feature sets in response to connection with a particular type of pump device, in accordance with some embodiments.

Referring now to FIG. 11, some embodiments of the controller device 200 can be configured to automatically enable or disable features related to delivery of particular medicines in response to a connection between the controller device and a particular type of pump device 100. As previously described, the controller device 200 in this embodiment is equipped with the control circuitry 240 that is programmed to offer a number of different feature sets to the user. The different features sets related to different medicines may be implemented, for example, in the user interface 220 of the controller device 200 including different status display information, different basal and bolus options, different calculator, historical data reporting options, and the like. Thus, each controller device 200 can be configured to connect with several different types of pump devices 100, such as a first type of pump device 10 that receives a first medicine therein and a second type of pump device 10 that receives a second medicine therein. The particular type of pump device 100 can be defined by an electronic indicator, for example, a parameter setting stored in the internal circuit 115 housed in the pump device 100 (e.g., internally stored on an internal memory chip, an identification circuit, or the like). As previously described, this parameter setting may be a permanent setting that is established by the supplier. The pump body 110 may also carry a label, bar code, or other physical indicator that identifies which type of medicine should be inserted into the pump cavity 116. In particular embodiments, the different types of pump devices 100 can have substantially the same shape and size, so the different types of pump devices 100 may different from one another only in the parameter setting stored in the internal circuit 115. Alternatively, the different types of pump devices may also include differently shaped internal cavities 116 (FIG. 1) so that the first type of pump device 100 receives a medicine cartridge having a different size or shape from a second medicine cartridge to be received by a second type of pump device 100.

In this embodiment, the controller device 200 is configured to provide a first feature set delivery of a first medicine (e.g., insulin), a second feature set related to delivery of a second medicine (e.g., morphine), and a third feature set related to delivery of a third medicine. It should be understood from the description herein that the controller device 200 can be programmed in advanced to provide different user interface options that are customized to each particular type of medicine. In such circumstances, the controller device 200 can be triggered to automatically (e.g., without manual user intervention) display the designated user interface options in response to attachment of a particular type of pump device carrying the designated medicine.

In one example, if the pump device 100 is a first type of pump (e.g., a parameter setting of pump type "A"), the controller device 200 is configured to automatically activate the feature set related to dispensation of insulin in response to the controller device 200 being connected with the first type of pump device 100. In such circumstances, the controller device 200 may activate the user interface display 222 to provide a number of menu options that are customized for delivery of insulin. For example, the user interface 220 can provide basal profile options and bolus delivery options specifically tailored to the pharmakinetic characteristics of the insulin medication. Likewise, the display screen 222 of the controller device 200 may display insulin treatment information (e.g., insulin basal rate, blood glucose level, etc.) during idle periods when no buttons 224 are actuated. Further, the user interface 220 of the controller device 200 may output an alert to notify the user of which type of medicine is prepared for delivery from the connected pump device 100.

In a second example, if the pump device 100 is a second type of pump (e.g., a parameter setting of pump type "B"), the controller device 200 is configured to automatically activate the feature set related to dispensation of a different medication (morphine in this embodiment) in response to the controller device 200 being connected with the second type of pump device 100. In such circumstances, the controller device 200 may activate the user interface display 222 to provide a number of menu options that are customized for delivery of the second medication. For example, the user interface 220 can provide basal profile options and bolus delivery options specifically tailored to the pharmakinetic characteristics of the morphine medication. Likewise, the display screen 222 of the controller device 200 may display morphine treatment information (e.g., combined dosage amounts, amount of time until next bolus dosages is available, etc.) during idle periods when no buttons 224 are actuated. Also, the user interface 220 of the controller device 200 may output an alert to notify the user of which type of medicine is prepared for delivery from the connected pump device 100.

Figure 12:
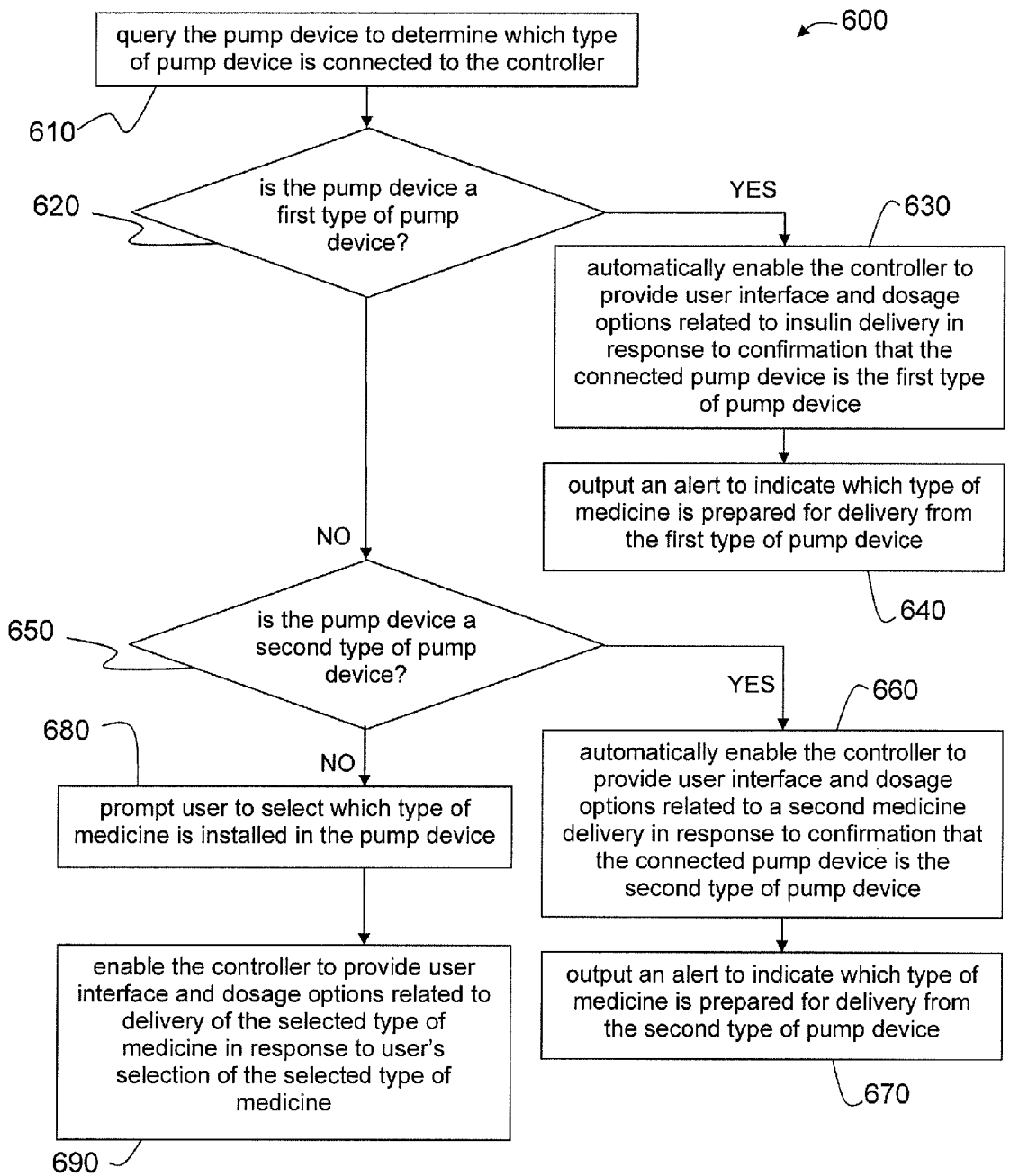
FIG. 12 is a flow chart of a process for using the infusion pump system of FIG. 11, in accordance with some embodiments.

Referring now to FIG. 12, some embodiments of the infusion pump system 10 can be used in a process 600 wherein the controller device 200 is configured to connect with multiple different types of pump devices 110 that contain different medicines, respectively. For example, as described in connection with FIG. 11, the controller device 200 may be equipped with control circuitry 240 (described in connection with FIG. 7) that is programmed in advanced to offer a number of different user interface options customized to different types of particular medicines. In this example process 600, the operation 610 can be performed to by the controller device 200 to query the pump device 100 to determine which type of pump device is connected to the controller device 200. For example, as previously described in connection with FIG. 11, the pump device 100 may include an electronic indicator (e.g., a parameter setting stored in an internal circuit 115 housed in the pump device 100) that is detected by the control circuitry 240 in response to connection between the pump device 100 and the controller device 200.

If the controller device 200 determines in operation 620 that the connected pump device 100 is a first type of pump device 100 (e.g., a parameter setting of "A"), the process 600 continues to operation 630. In operation 630, the controller device 200 may automatically (e.g., without manual intervention by the user) enable the controller to provide a feature set specifically for a first type of medicine (insulin in this embodiment). For example, the controller device 200 may automatically activate the user interface 220 so as to provide dosage and menu options related to insulin delivery. In operation 640, the controller device 200 can output an alert indicative of which type of medicine (insulin in this example) is prepared for delivery from the connected pump device 100.

Still referring to FIG. 10, if the controller device 200 determines in operation 650 that the connected pump device 100 is a second type of pump device 100 (e.g., a parameter setting of "B"), the process 600 continues to operation 660. In operation 660, the controller device 200 may automatically enable the controller to provide a feature set specifically for a second type of medicine (morphine in this embodiment). For example, the controller device 200 may automatically activate the user interface 220 so as to provide dosage and menu options related to morphine delivery. In operation 670, the controller device 200 can output an alert indicative of which type of medicine (morphine in this example) is prepared for delivery from the connected pump device 100.

If the controller device 200 determines in operation 650 that the connected pump device 100 is a not a first or second type of pump device 100 (e.g., a parameter setting different than "A" or "B"), the process 600 continues to operation 680. In operation 680, the controller device 200 may automatically enable the user interface 220 to prompt the user to select which type of medicine is installed in the connected pump device 100. For example, the controller device 200 may display an alert that includes a list of medicine types so that the user can scroll through the list on the display 222 and select the proper type of medicine. In response to the user's selection, operation 690 can be performed so that the controller device 200 automatically enables the user interface to provide a feature set specifically for the selected type of medicine. For example, the controller device 200 may automatically activate the user interface 220 so as to provide dosage and menu options related to selected medicine.

Accordingly, the some embodiments of the controller device 200 can be configured to automatically activate selected features related to a first medicine type (e.g., a user interface and dosage options related to insulin delivery) only in response to a first type of pump device being connected to the controller device. Optionally, the controller device may automatically disable selected features related to insulin delivery in response to a second type of pump device being connected to the controller device. Thus, the controller can be configured to control dosages of multiple different types of medicines, and the controller's user interface and dosage options can be automatically adjusted based upon the particular type of pump device that is connected therewith.

A number of embodiments have been described. Nevertheless, it will be understood that various modifications may be made without departing from the spirit and scope of this disclosure. For example, the controller device can be configured to automatically enable or disable feature sets other than those specifically illustrated herein, in response to connection with a particular type of pump device. Accordingly, other embodiments are within the scope of the following claims.

What is claimed is:

1. A method of using a portable infusion pump system, comprising:

selecting an insulin pump device from a set of insulin pump devices comprising at least a first type of insulin pump device and a second type of insulin pump device having the same size and shape as the first type of insulin pump device, wherein the first type of insulin pump device houses a drive system configured to dispense insulin and an internal circuit that stores a first parameter setting indicative of disabling wireless communication, and wherein the second type of insulin pump device houses a drive system configured to dispense insulin and an internal circuit that stores a second parameter setting indicative of enabling wireless communication; and removably attaching the first type of insulin pump device to a controller device to form an electrical connection between the controller device and the first type of insulin pump device so that the controller device is operable to control the drive system of the first type of insulin pump device to dispense insulin from the first type of insulin pump device, wherein the controller device automatically disables a wireless communication device of the controller device in response to querying via the electrical connection the first parameter setting of the internal circuit housed by the first type of insulin pump device, and wherein the controller device displays a text alert message on a user interface display of the controller device indicating that wireless communication is disabled.

2. The method of claim 1, further comprising:

detaching the first type of insulin pump device from the controller device; and removably attaching the second type of insulin pump device to the controller device to form an electrical connection between the controller device and the second type of insulin pump device so that the controller device is operable to control the drive system of the second type of insulin pump device to dispense insulin from the second type of insulin pump device, wherein the controller device automatically enables the wireless communication device of the controller device in response to querying the second parameter setting of the internal circuit housed by the second type of insulin pump device.

3. The method of claim 1, wherein the controller device displays the text alert message on the user interface of the controller device indicating that wireless communication is disabled until the second type of insulin pump device is removably attached to the controller device.

4. The method of claim 1, wherein the wireless communication device is housed inside the controller device, and wherein the wireless communication device is configured to wirelessly communicate with at least one of a body-worn glucose monitoring device and a blood glucose meter.

5. The method of claim 1, wherein the set of insulin pump devices comprises at least the first type of insulin pump device, the second type of insulin pump device, and a third type of insulin pump device, and wherein the controller device automatically changes to a training mode user interface in response to the electrical connection with the third type insulin pump device.

6. The method of claim 1, wherein the controller device includes control circuitry that is configured to provide an advanced feature set related to continuous glucose monitoring, the advanced feature set including: activation of the wireless communication device to communicate with a body-worn glucose monitoring device, and activation of the user interface display of the controller device to display a glucose level in response to receiving data from the body-worn glucose monitoring device.

7. A method of controlling a portable infusion pump system, comprising:
establishing an electrical connection with an insulin pump device selected from a set of insulin pump devices comprising at least a first type of insulin pump device and a second type of insulin pump device having the same size and shape as the first insulin pump device, wherein the first type of insulin pump device houses an internal circuit that stores a first parameter setting indicative of enabling a first feature set, and wherein the second type of insulin pump device houses an internal circuit that stores a second parameter setting indicative of disabling the first feature set, wherein the selected insulin pump device is removably mounted to a controller device when the electrical connection is established so that the controller device is operable to control dispensation of insulin from the selected insulin pump device;
querying the selected insulin pump device via the electrical connection to determine whether the selected insulin pump device is any one of the first type of insulin pump device or the second type of insulin pump device;
automatically disabling the first feature set provided by the controller device in response to the controller device recognizing that the selected insulin pump device is the second type of insulin pump device; and
outputting a text alert message via the user interface of the controller device indicating that the first feature set is disabled,
wherein outputting the text alert message on the user interface of the controller device comprises displaying a visual message indicating at least one of disablement of wireless communication and disablement of a drive system of the selected insulin pump device.

8. A method of controlling a portable infusion pump system, comprising:
establishing an electrical connection with an insulin pump device selected from a set of insulin pump devices comprising at least a first type of insulin pump device and a second type of insulin pump device having the same size and shape as the first insulin pump device, wherein the first type of insulin pump device houses an internal circuit that stores a first parameter setting indicative of enabling a first feature set, and wherein the second type of insulin pump device houses an internal circuit that stores a second parameter setting indicative of disabling the first feature set, wherein the selected insulin pump device is removably mounted to a controller device when the electrical connection is established so that the controller device is operable to control dispensation of insulin from the selected insulin pump device;
querying the selected insulin pump device via the electrical connection to determine whether the selected insulin pump device is any one of the first type of insulin pump device or the second type of insulin pump device;
automatically disabling the first feature set provided by the controller device in response to the controller device recognizing that the selected insulin pump device is the second type of insulin pump device; and
outputting a text alert message via the user interface of the controller device indicating that the first feature set is disabled,
wherein the controller device includes control circuitry that is configured to provide the first feature set related to continuous glucose monitoring, the first feature set including: activation of a wireless communication device to communicate with a body-worn glucose monitoring device, and activation of a user interface display of the controller device to display a glucose level in response to receiving data from the body-worn glucose monitoring device.

9. A portable infusion pump system, comprising:
a set of insulin pump devices comprising at least a first type of insulin pump device and a second type of insulin pump device having the same size and shape as the first type of insulin pump device, wherein the first type of insulin pump device houses an internal circuit that stores a first parameter setting indicative of disabling wireless communication, wherein the second type of insulin pump device houses an internal circuit that stores a second parameter setting indicative of enabling wireless communication, and wherein each respective insulin pump device of the set of insulin pump devices includes: an insulin pump housing that defines a space to receive insulin, and a drive system to dispense the insulin from the respective insulin pump device when the medicine is received in the space of the insulin pump housing; and
a controller device removably attachable to each respective insulin pump device of the set of insulin pump devices so as to electrically connect with the respective insulin pump device and control dispensation of the insulin from the insulin pump device, wherein the controller device is configured to automatically enable a first feature set provided by the controller device in response to the controller device recognizing that a removably attached insulin pump device of the set of insulin pump devices is the first type of insulin pump device, and wherein the controller device is configured to automatically disable the first feature set provided by the controller device in response to the controller device recognizing that the removably attached insulin pump device of the set of insulin pump devices is the second type of insulin pump device, wherein in response to the controller device recognizing that the removably attached insulin pump device of the set of insulin pump devices is the second type of insulin pump device, the controller device outputs a text alert message via a user interface of the controller device indicating that the first feature set is disabled,
wherein the controller device outputs the text alert message via the user interface by displaying a visual message indicating at least one of disablement of wireless communication and disablement of a drive system of the insulin pump device.

10. A portable infusion pump system, comprising:
a set of insulin pump devices comprising at least a first type of insulin pump device and a second type of insulin pump device having the same size and shape as the first type of insulin pump device, wherein the first type of insulin pump device houses an internal circuit that stores a first parameter setting indicative of disabling wireless communication, wherein the second type of insulin pump device houses an internal circuit that stores a second parameter setting indicative of enabling wireless communication, and wherein each respective insulin pump device of the set of insulin pump devices includes:

an insulin pump housing that defines a space to receive insulin, and a drive system to dispense the insulin from the respective insulin pump device when the medicine is received in the space of the insulin pump housing; and a controller device removably attachable to each respective insulin pump device of the set of insulin pump devices so as to electrically connect with the respective insulin pump device and control dispensation of the insulin from the insulin pump device, wherein the controller device is configured to automatically enable a first feature set provided by the controller device in response to the controller device recognizing that a removably attached insulin pump device of the set of insulin pump devices is the first type of insulin pump device, and wherein the controller device is configured to automatically disable the first feature set provided by the controller device in response to the controller device recognizing that the removably attached insulin pump device of the set of insulin pump devices is the second type of insulin pump device, wherein in response to the controller device recognizing that the removably attached insulin pump device of the set of insulin pump devices is the second type of insulin pump device, the controller device outputs a text alert message via a user interface of the controller device indicating that the first feature set is disabled, wherein the controller device includes control circuitry that is configured to provide the first feature set related to continuous glucose monitoring, the first feature set including: activation of a wireless communication device to communicate with a body-worn glucose monitoring device, and a display of a glucose level via the user interface of the controller device in response to receiving data from the body-worn glucose monitoring device.

11. A portable infusion pump system, comprising:

a set of insulin pump devices comprising at least a first type of insulin pump device and a second type of insulin pump device having the same size and shape as the first type of insulin pump device, wherein the first type of insulin pump device houses an internal circuit that stores a first parameter setting indicative of disabling wireless communication, wherein the second type of insulin pump device houses an internal circuit that stores a second parameter setting indicative of enabling wireless communication, and wherein each respective insulin pump device of the set of insulin pump devices includes:

an insulin pump housing that defines a space to receive insulin, and a drive system to dispense the insulin from the respective insulin pump device when the medicine is received in the space of the insulin pump housing; and a controller device removably attachable to each respective insulin pump device of the set of insulin pump devices so as to electrically connect with the respective insulin pump device and control dispensation of the insulin from the insulin pump device, wherein the controller device is configured to automatically enable a first feature set provided by the controller device in response to the controller device recognizing that a removably attached insulin pump device of the set of insulin pump devices is the first type of insulin pump device, and wherein the controller device is configured to automatically disable the first feature set provided by the controller device in response to the controller device recognizing that the removably attached insulin pump device of the set of insulin pump devices is the second type of insulin pump device, wherein in response to the controller device recognizing that the removably attached insulin pump device of the set of insulin pump devices is the second type of insulin pump device, the controller device outputs a text alert message via a user interface of the controller device indicating that the first feature set is disabled, wherein the controller device includes control circuitry that is configured to provide the first feature set related to wireless communication with a blood glucose meter, wherein the controller device automatically activates the first feature set related to wireless communication with a blood glucose meter in response to the controller device recognizing that the removably attached insulin pump device of the set of insulin pump devices is the first type of insulin pump device.

* * * * *

UNITED STATES PATENT AND TRADEMARK OFFICE
CERTIFICATE OF CORRECTION

PATENT NO. : 9,132,234 B2
APPLICATION NO. : 13/760596
DATED : September 15, 2015
INVENTOR(S) : Estes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 218 days.

Signed and Sealed this
Twelfth Day of April, 2016

Michelle K. Lee
*Director of the United States Patent and Trademark Office*